US012605519B2

(12) United States Patent
Eger et al.

(10) Patent No.: US 12,605,519 B2
(45) Date of Patent: Apr. 21, 2026

(54) PROCESS AND SIGNAL PROCESSING UNIT FOR DETERMINING THE BREATHING ACTIVITY OF A PATIENT

(71) Applicant: Drägerwerk AG & Co. KGaA, Lübeck (DE)

(72) Inventors: Marcus Eger, Lübeck (DE); Thomas Handzsuj, Lübeck (DE); Philipp Rostalski, Lübeck (DE); Eike Petersen, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1034 days.

(21) Appl. No.: 17/760,573

(22) PCT Filed: Sep. 7, 2020

(86) PCT No.: PCT/EP2020/074893
§ 371 (c)(1),
(2) Date: Mar. 15, 2022

(87) PCT Pub. No.: WO2021/052791
PCT Pub. Date: Mar. 25, 2021

(65) Prior Publication Data
US 2022/0339382 A1     Oct. 27, 2022

(30) Foreign Application Priority Data
Sep. 16, 2019     (DE) ......................... 102019006480.1

(51) Int. Cl.
*A61M 16/00*     (2006.01)
(52) U.S. Cl.
CPC ...... *A61M 16/024* (2017.08); *A61M 16/0003* (2014.02); *A61M 2016/0027* (2013.01)

(58) Field of Classification Search
CPC ............ A61M 16/024; A61M 16/0003; A61M 2016/0027; A61M 16/026; A61M 16/022;
(Continued)

(56) References Cited

U.S. PATENT DOCUMENTS

| | | | |
|---|---|---|---|
| 6,588,423 B1 | 7/2003 | Sinderby | |
| 7,021,310 B1 | 4/2006 | Sinderby et al. | |

(Continued)

FOREIGN PATENT DOCUMENTS

| | | |
|---|---|---|
| CN | 105916440 A | 8/2016 |
| CN | 109069030 A | 12/2018 |

(Continued)

OTHER PUBLICATIONS

PE2E Translation Albanese CN_109906054 (Year: 2019).*
(Continued)

*Primary Examiner* — Victoria Murphy
*Assistant Examiner* — Sydney Reyes Russell
(74) *Attorney, Agent, or Firm* — McGlew and Tuttle, P.C.

(57) ABSTRACT

A process and a signal processing unit for determining a first pneumatic indicator ($P_{mus,1}$) and a second pneumatic indicator ($P_{mus,2}$) for the breathing activity of a patient, wherein the two values describe the activity of two different regions of the respiratory system. In one alternative of the present invention, two respiratory signals ($Sig_1$, $Sig_2$) are generated from measured values. The two values ($P_{mus,1}$, $P_{mus,2}$) are determined with the use of these respiratory signals ($Sig_1$, $Sig_2$) and of a predefined function (Fkt) and of predefined relationships ($Zus_1$, $Zus_2$).

19 Claims, 10 Drawing Sheets

(58) Field of Classification Search
CPC ....... A61B 5/0816; A61B 5/085; A61B 5/087;
A61B 5/091
See application file for complete search history.

(56) References Cited

U.S. PATENT DOCUMENTS

| | | | |
|---|---|---|---|
| 9,114,220 B2 | 8/2015 | Masic | |
| 2002/0056454 A1 | 5/2002 | Samzelius | |
| 2004/0040560 A1* | 3/2004 | Euliano ................. | A61B 5/082 |
| | | | 128/204.23 |
| 2008/0308104 A1 | 12/2008 | Blomberg et al. | |
| 2009/0114224 A1 | 5/2009 | Handzsuj et al. | |
| 2009/0159082 A1 | 6/2009 | Eger | |
| 2010/0078026 A1* | 4/2010 | Andrieux ......... | A61M 16/0465 |
| | | | 128/204.21 |
| 2011/0301482 A1 | 12/2011 | Sinderby et al. | |
| 2013/0213399 A1 | 8/2013 | Hansmann et al. | |
| 2016/0310069 A1 | 10/2016 | Sinderby et al. | |
| 2017/0119984 A1 | 5/2017 | Bahns et al. | |
| 2017/0128684 A1 | 5/2017 | Sinderby et al. | |
| 2017/0326315 A1 | 11/2017 | Mulqueeny et al. | |
| 2018/0344194 A1 | 12/2018 | Eger et al. | |
| 2019/0274586 A1 | 9/2019 | Höskuldsson et al. | |
| 2022/0160255 A1 | 5/2022 | Eger et al. | |

FOREIGN PATENT DOCUMENTS

| | | | | | |
|---|---|---|---|---|---|
| CN | 109906054 A | * | 6/2019 | .............. | A61B 5/03 |
| DE | 102012003509 A1 | | 8/2013 | | |
| DE | 102015011390 A1 | | 3/2017 | | |
| DE | 102015014106 A1 | | 5/2017 | | |
| DE | 102015015296 A1 | * | 6/2017 | ............. | A61B 5/087 |
| DE | 102007062214 C5 | | 12/2017 | | |
| WO | 199722377 A1 | | 6/1997 | | |
| WO | 2012024733 A2 | | 3/2012 | | |
| WO | WO-2017113017 A1 | * | 7/2017 | .......... | A61B 5/0488 |
| WO | WO-2018143844 A1 | * | 8/2018 | ............. | A61B 5/087 |

OTHER PUBLICATIONS

EspaceNet Translation Eger DE_102015015296 (Year: 2017).*
"Sternomastoid, rib cage, and expiratory muscle activity during weaning failure", Parthasarathy et al., J Appl Physiol 103: 140-147, 2007. First published Mar. 29, 2007; doi:10.1152/japplphysiol.00904. 2006. pp. 140-147.
"Ultrasound Sensors for Diaphragm Motion Tracking: An Application in Non-Invasive Respiratory Monitoring", Shahshahani et al., Sensors 2018, 8, 2617; doi:10.3390/s18082617 www.mdpi.com/journal/sensors. pp. 1-21.
"Neural control of mechanical ventilation in respiratory failure", Sinderby et al., © 1999 Nature America Inc. • http://medicine.nature. com. Nature Medicine • vol. 5 • No. 12 • Dec. 1999. pp. 1433-1436.
"Proportional Assist Ventilation", Magdy Younes, Part V Alternative Methods of Ventilator Support, chapter 15. pp. 349-369.
"Is One Fixed Level of Assist Sufficient to Mechanically Ventilate Spontaneously Breathing Patients?", Sinderby et al., pp. 348-357.
"Clinical Manifestations of Inspiratory Muscle Fatigue", Cohen et al., Clinical Studies, Sep. 1982 The American Journal of Medicine vol. 73. pp. 308-316.
"Inspiratory Muscle Unloading by Neurally Adjusted Ventilatory Assist During Maximal Inspiratory Efforts in Healthy Subjects", Sinderby et al., www.chestjournal.org Chest / 131 / 3 / Mar. 2007. pp. 711-717.

* cited by examiner

PROCESS AND SIGNAL PROCESSING UNIT FOR DETERMINING THE BREATHING ACTIVITY OF A PATIENT

CROSS REFERENCE TO RELATED APPLICATIONS

This application is a United States National Phase Application of International Application PCT/EP2020/074893, filed Sep. 7, 2020, and claims the benefit of priority under 35 U.S.C. § 119 of German Application 102019006480.1, filed Sep. 16, 2019, the entire contents of which are incorporated herein by reference.

TECHNICAL FIELD

The present invention pertains to a process and to a signal processing unit for determining the respective breathing activity of a first region and of a second region of the respiratory system of a patient. The results of the determination may be used, e.g., to control a mechanical ventilator.

TECHNICAL BACKGROUND

A process and a device for generating two data signals are described in DE 102015015296 A1, wherein the first data signal describes an activity of a muscle responsible for inhalation and the second data signal describes an activity of a muscle relevant for exhalation. Two surface myography sensors on the skin of the patient detect two EMG signals. A heartbeat component in the EMG signals is compensated by calculation. In addition, the breathing activity of the patient is determined. A computer detects on the basis of the detected breathing activity when the patient is inhaling and when he is exhaling. A first separated signal and a second separated signal are determined on the basis of the two EMG signals.

SUMMARY

The basic object of the present invention is to provide a computer-implemented process and a signal processing unit, by means of which the intrinsic breathing activity of a patient is determined more specifically than by prior-art processes and signal processing units, and it can be supported more specifically by a ventilator when needed.

The object is accomplished by a process having the features of determining a first pneumatic indicator ($P_{mus,1}$) and a second pneumatic indicator ($P_{mus,2}$) for the breathing activity of a patient (P), wherein the first pneumatic indicator ($P_{mus,1}$) describes activity of a first region of a respiratory system of the patient (P) and/or of a first process during breathing by the patient (P) and the second pneumatic indicator ($P_{mus,2}$) describes activity of a second region of the respiratory system of the patient (P) and/or of a second process during breathing by the patient (P), wherein a function (Fkt), which describes a measurable and preferably pneumatic indicator ($P_{aw}$, $P_{es}$) for an airway pressure, wherein the airway pressure is achieved by an overall intrinsic breathing activity of the patient plus an optional mechanical ventilation of the patient (P), is predefined in a computer-accessible form as a function of at least:

an indicator for a volume flow (Vol') of breathing air relative to the patient (P) and/or an indicator for a filling level of the lungs (Vol) of the patient (P) as well as a function of the two pneumatic indicators ($P_{mus,1}$, $P_{mus,2}$) to be determined and/or of an overall pneumatic indicator ($P_{mus}$) for the overall breathing activity of the patient (P), wherein a first relationship ($Zus_1$) between the first pneumatic indicator ($P_{mus,1}$) and at least one first measurable respiratory signal ($Sig_1$) and/or a second relationship ($Zus_2$) between the second pneumatic indicator ($P_{mus,2}$) and at least one second measurable respiratory signal ($Sig_2$) and/or an overall relationship (Zus) between the overall pneumatic indicator ($P_{mus}$) for the overall breathing activity of the patient (P) and at least one measurable overall respiratory signal (Sig)

are predefined in a computer-accessible form, wherein at least one of the first and second relationships ($Zus_1$, $Zus_2$) or the overall relationship (Zus) have at least one model parameter (k, $k_1$, $k_2$) and wherein the process comprises the steps that the patient (P) is connected at least temporarily to an airway pressure sensor, which measures the indicator for the airway pressure ($P_{aw}$, $P_{es}$), a signal processing unit receives measured values of the airway pressure sensor when the patient (P) is connected to the airway pressure sensor and generates an airway pressure signal ($P_{aw}$, $P_{es}$) using values measured by the airway pressure sensor and uses a predefined value for the airway pressure ($P_{aw}$, $P_{es}$) as an airway pressure signal ($P_{aw}$, $P_{es}$) when the patient (P) is not connected to the airway pressure sensor, the signal processing unit receives measured values (RM) from a volume flow sensor, which measures an indicator for the volume flow of breathing air, and generates a volume flow signal (Vol') from values (RM) measured by the volume flow sensor, and/or receives measured values (RM) from a filling level sensor, which measures an indicator for the filling level of the lungs, and generates a volume signal (Vol) from values (RM) measured by the filling level sensor, at least one of the following three sequences are carried out, wherein in the first sequence the signal processing unit receives measured values (RM) from a first breathing sensor, wherein these measured values pertain to an indicator that is correlated with the first pneumatic indicator ($P_{mus,1}$), generates the first respiratory signal ($Sig_1$) from values (RM) measured by the first breathing sensor, derives a respective value $\{k_{1,est}t_i\}$ for the model parameter or each model parameter ($k_1$), which occurs in the first relationship, with the use of the predefined function (Fkt) and of generated signals ($P_{aw}$, Vol', Vol, $Sig_1$), which signals occur in the function (Fkt), and determines the first pneumatic indicator ($P_{mus,1}$) with the use of the first relationship ($Zus_1$) and of the derived value or at least one derived value $\{k_{1,est}(t_i)\}$ of a model parameter $\{k_{1,est}\}$ occurring in the first relationship ($Zus_1$), in the second sequence the signal processing unit receives measured values (RM) from a second breathing sensor, wherein the measured values pertain to an indicator that is correlated with the second pneumatic indicator $(P_{mus,2})$, generates the second respiratory signal $(Sig_2)$ from values measured by the second breathing sensor, derives a respective value $\{k_{2,est}(t_i)\}$ for the model parameter or each model parameter $(k_2)$ that occurs in the second relationship $(Zus_2)$ with the use of the predefined function (Fkt) and of generated signals $(P_{aw}, Vol', Vol, Sig_2)$, which signals occur in the function (Fkt), and determines the second pneumatic indicator $(P_{mus,2})$ with the use of the second relationship $(Zus_2)$ and of the derived value or at least one derived value $\{k_{2,est}(t_i)\}$ of a model parameter $\{k_{2,est}\}$ occurring in the second relationship $(Zus_2)$, in the third sequence the signal processing unit receives measured values (RM) from an overall breathing sensor, wherein the measured values pertain to an indicator that is correlated with the overall pneumatic indicator $(P_{mus})$, generates the overall respiratory signal (Sig) from values measured by the overall breathing sensor, derives a respective value $\{k_{est}(t_i)\}$ for the model parameter or each model parameter (k) that occurs in the overall relationship (Zus) with the use of the predefined function (Fkt) and of generated signals $(P_{aw}, Vol', Vol, Sig)$, which signals occur in the function (Fkt), and determines the overall pneumatic indicator $(P_{mus})$ with the use of the overall relationship (Zus) and of the derived model parameter value or each derived model parameter value $\{k_{est}(t_i)\}$, in the case that one pneumatic indicator $(P_{mus,1}, P_{mus,2})$ and the overall pneumatic indicator $(P_{mus})$ have been determined, but the other pneumatic indicator $(P_{mus,2}, P_{mus,1})$ has not been determined, the signal processing unit determines the other pneumatic indicator $(P_{mus,2}, P_{mus,1})$ with the use of the one pneumatic indicator $(P_{mus,1}, P_{mus,2})$ already determined and of the determined overall pneumatic indicator $(P_{mus})$, in the case that the one pneumatic indicator $(P_{mus,1}, P_{mus,2})$ has been determined but neither the overall pneumatic indicator $(P_{mus})$ nor the other pneumatic indicator $(P_{mus,2}, P_{mus,1})$ has been determined, the signal processing unit determines the overall pneumatic indicator $(P_{mus})$ with the use of the already determined pneumatic indicator $(P_{mus,1}, P_{mus,2})$ as well as of the volume flow signal (Vol') and/or of the volume signal (Vol) and/or of a predefined percentage function (p1, p2), and determines the other pneumatic indicator $(P_{mus,2}, P_{mus,1})$ with the use of the already determined pneumatic indicator $(P_{mus,1}, P_{mus,2})$ and of the overall pneumatic indicator $(P_{mus})$, and in the case that the overall pneumatic indicator $(P_{mus})$ has been determined, but neither the first pneumatic indicator $(P_{mus,1})$ nor the second pneumatic indicator $(P_{mus,2})$ has been determined, the signal processing unit determines the first pneumatic indicator $(P_{mus,1})$ and the second pneumatic indicator $(P_{mus,2})$ with the use of the overall pneumatic indicator $(P_{mus})$ as well as of the volume flow signal (Vol') and/or of the volume signal (Vol) and/or of a predefined percentage function (p1, p2).

The object of the present invention is also accomplished by a signal processing unit having the features of determining by calculation first pneumatic indicator $(P_{mus,1})$ and a second pneumatic indicator $(P_{mus,2})$ for the breathing activity of a patient (P), wherein the first pneumatic indicator $(P_{mus,1})$ describes activity of a first region of a respiratory system of the patient (P) and/or of a first process during breathing by the patient (P) and the second pneumatic indicator $(P_{mus,2})$ describes activity of a second region of the respiratory system of the patient (P) and/or of a second process during the breathing by the patient (P), wherein the signal processing unit (5) has at least temporarily reading access to a memory (9), in which a function (Fkt) is stored in a computer-accessible form, wherein the function (Fkt) describes a measurable and preferably pneumatic indicator $(P_{aw}, P_{es})$ for an airway pressure, wherein the airway pressure is achieved by the overall intrinsic breathing activity of the patient plus an optional mechanical ventilation of the patient (P), as a function of at least an indicator for the volume flow (Vol') of breathing air relative to the patient (P) and/or an indicator for the filling level of the lungs (Vol) of the patient (P) as well as a function of the two pneumatic indicators $(P_{mus,1}, P_{mus,2})$ to be determined and/or of an overall pneumatic indicator $(P_{mus})$ for the overall breathing activity of the patient (P), wherein furthermore a predefined first relationship $(Zus_1)$ between the first pneumatic indicator $(P_{mus,1})$ and at least one first measurable respiratory signal $(Sig_1)$ and/or a predefined second relationship $(Zus_2)$ between the second pneumatic indicator $(P_{mus,2})$ and at least one second measurable respiratory signal $(Sig_2)$ and/or a predefined overall relationship (Zus) between the overall pneumatic indicator $(P_{mus})$ for the overall breathing activity of the patient (P) and at least one measurable overall respiratory signal (Sig)

are stored in the memory in a computer-accessible form, wherein at least one of the first and second relationships $(Zus_1, Zus_2)$ or the overall relationship (Zus) has at least one model parameter $(k, k_1, k_2)$ and wherein the patient (P) can be connected or is at least temporarily connected to an airway pressure sensor, which is configured to measure the indicator for the airway pressure $(P_{aw}, P_{es})$, wherein the signal processing unit is configured to receive measured values from the airway pressure sensor when the patient (P) is connected to the airway pressure sensor and to generate an airway pressure signal $(P_{aw}, P_{es})$ with the use of values measured by the airway pressure sensor and to use a predefined value for the airway pressure $(P_{aw}, P_{es})$ as an airway pressure signal $(P_{aw}, P_{es})$ when the patient (P) is not connected to the airway pressure sensor, wherein the signal processing unit is configured to receive measured values (RM) from a volume flow sensor, which is configured to measure a value for the volume flow of breathing air, and to generate a volume flow signal (Vol') from values (RM) measured by the volume flow sensor and/or to receive measured values (RM) from a filling level sensor, which is configured to measure a value for the filling level of the lungs, and to generate a volume signal (Vol) from values (RM) measured by the filling level sensor, wherein the signal processing unit is configured to carry out a first and/or a second and/or a third sequence, wherein the first sequence comprises the steps that the signal processing unit receives measured values (RM) from a first breathing sensor wherein these measured values pertain to an indicator that is correlated with the first pneumatic indicator ($P_{mus,1}$), generates the first respiratory signal ($Sig_1$) from values (RM) measured by the first breathing sensor, derives a respective value $\{k_{1,est}(t_i)\}$ for the model parameter or for each model parameter ($k_1$), which occurs in the first relationship ($Zus_1$), with the use of the predefined function (Fkt) and of generated signals ($P_{aw}$, Vol', Vol, $Sig_1$), which signals occur in the function (Fkt), determines the first pneumatic indicator ($P_{mus,1}$) with the use of the first relationship ($Zus_1$) and of the derived value or at least one derived value $\{k_{1,est}(t_i)\}$ of a model parameter $\{k_{1,est}\}$ occurring in the first relationship ($Zus_1$) and wherein the second sequence comprises the steps that the signal processing unit receives measured values (RM) from a second breathing sensor, wherein these measured values pertain to an indicator that is correlated with the second pneumatic indicator ($P_{mus,2}$), generates the second respiratory signal ($Sig_2$) from values measured by the second breathing sensor, derives a respective value $\{k_{2,est}(t_i)\}$ for the model parameter or for each model parameter ($k_2$), which occurs in the second relationship ($Zus_2$), with the use of the function (Fkt) and of generated signals ($P_{aw}$, Vol', Vol, $Sig_2$), which signals occur in the function (Fkt), and determines the second pneumatic indicator ($P_{mus,2}$) with the use of the second relationship ($Zus_2$) and of the derived value or of at least one derived value $\{k_{2,est}(t_i)\}$ of a model parameter $\{k_{2,est}\}$ occurring in the second relationship ($Zus_2$), wherein the third sequence comprises the steps that the signal processing unit receives measured values (RM) from an overall breathing sensor, wherein the measured values pertain to an indicator that is correlated with the overall pneumatic indicator ($P_{mus}$), generates the overall respiratory signal (Sig) from values measured by the overall breathing sensor, derives a respective value $\{k_{est}(t_i)\}$ for the model parameter or for each model parameter (k), which occurs in the overall relationship (Zus), with the use of the function (Fkt) and of generated signals ($P_{aw}$, Vol', Vol, Sig), which signals occur in the function (Fkt), and determines the overall pneumatic indicator ($P_{mus}$) with the use of the overall relationship (Zus) and of the derived model parameter value or of each derived model parameter value $\{k_{est}(t_i)\}$ which occur in the overall relationship (Zus), wherein the signal processing unit is configured to determine the other pneumatic indicator ($P_{mus,2}$, $P_{mus,1}$) with the use of the one, already determined pneumatic indicator ($P_{mus,1}$, $P_{mus,2}$) and of the determined overall pneumatic indicator ($P_{mus}$) in the case that the one pneumatic indicator ($P_{mus,1}$, $P_{mus,2}$) and the overall pneumatic indicator ($P_{mus}$) have been determined but the other pneumatic indicator ($P_{mus,2}$, $P_{mus,1}$) has not been determined, in the case that the one pneumatic indicator ($P_{mus,1}$, $P_{mus,2}$) has been determined but neither the overall pneumatic indicator ($P_{mus}$) nor the other pneumatic indicator ($P_{mus,2}$, $P_{mus,1}$) has been determined, the signal processing unit is configured to determine the overall pneumatic indicator ($P_{mus}$) with the use of the already determined pneumatic indicator ($P_{mus,1}$, $P_{mus,2}$) as well as of the volume flow signal (Vol') and/or of the volume signal (Vol) and/or of a predefined percentage function (p1, p2) and to determine the other pneumatic indicator ($P_{mus,2}$, $P_{mus,1}$) with the use of the already determined pneumatic indicator ($P_{mus,1}$, $P_{mus,2}$) and of the overall pneumatic indicator ($P_{mus}$), and the signal processing unit is configured to determine the first pneumatic indicator ($P_{mus,1}$) and the second pneumatic indicator ($P_{mus,2}$) with the use of the overall pneumatic indicator ($P_{mus}$) as well as of the volume flow signal (Vol') and/or of the volume signal (Vol) and/or of a predefined percentage function (p1, p2) in the case that the overall pneumatic indicator ($P_{mus}$) has been determined but neither the first pneumatic indicator ($P_{mus,1}$) nor the second pneumatic indicator ($P_{mus,2}$) have been determined.

Advantageous embodiments of the process according to the present invention are also corresponding advantageous embodiments of the signal processing unit according to the present invention and vice versa.

A first pneumatic indicator and a second pneumatic indicator are determined by the computer-implemented process according to the present invention, and a signal processing unit performs the determination automatically. Both pneumatic indicators pertain to the intrinsic breathing activity of a patient, which is also called spontaneous breathing. The signal processing unit according to the present invention is configured to determine a first pneumatic indicator and a second pneumatic indicator for the breathing activity of the patient. "Determination" of a pneumatic indicator is defined as the process of directly measuring or calculating at least one value for the indicator and of using signals that have been generated from measured values of sensors for calculating the indicator.

The first pneumatic indicator describes the activity of a first region of the respiratory system of the patient. Or else, the first pneumatic indicator describes a first process during the spontaneous breathing by the patient. The second pneumatic indicator describes the activity of a second region of the respiratory system or a second process during the spontaneous breathing. The two regions or the two processes are different from one another, and preferably they do not overlap in space and time. The two pneumatic indicators are correlated with the activities of the two regions of the respiratory system or of the two breathing processes.

Breathing generates an airway pressure, especially in front of the mouth and in the esophagus of the patient. A function is predefined in a computer-accessible form. This predefined function describes a measurable indicator for the airway pressure at a defined point as a function of at least one indicator for the volume flow of breathing air to the patient and/or of an indicator for the filling level of the lungs of the patient as well as of the two pneumatic indicators to be determined and/or of an overall pneumatic indicator for the overall breathing activity of the patient.

"At least" means that the function may contain additional indicators and/or additional measurable signals. The overall breathing activity of the patient comprises that of the first region and that of the second region and of the two processes. It may consist of these two regions/processes or comprise additional regions/processes.

Therefore, the following four alternatives are specified:
The airway pressure value is a function of the volume flow indicator and of the two pneumatic
indicators to be determined, or of the lung filling level indicator and of the two pneumatic
indicators to be determined, or of the volume flow indicator and of the overall pneumatic
indicator, or of the lung filling level indicator and of the overall
pneumatic indicator.

The measurable indicator for the airway pressure is preferably a pneumatic indicator. The overall breathing activity, which is described by the overall pneumatic indicator, comprises the activity of the two regions of the respiratory system or the two processes taking place during breathing.

The signal processing unit according to the present invention has at least temporarily reading access to a memory, in which this computer-accessible function is stored.

Furthermore, at least one of the following three relationships and optionally a plurality of these three relationships are predefined in a computer-accessible form:

a first relationship between the first pneumatic indicator to
be determined and at least one first measurable respiratory signal, a second relationship between the second pneumatic
indicator to be determined and at least one second
measurable respiratory signal or an overall relationship between the overall pneumatic
indicator for the overall breathing activity of the patient
and at least one measurable overall respiratory signal.

A respiratory signal corresponds to a breathing activity of the patient and can be measured pneumatically, electrically or in another suitable manner.

At least one of these three relationships has at least one model parameter, and optionally each used relationship does have one.

The relationship or each predefined relationship is likewise stored in the memory, to which the signal processing unit according to the present invention has reading access.

The patient can be connected to an airway pressure sensor or is connected at least temporarily to an airway pressure sensor. This airway pressure sensor measures the indicator for the airway pressure, which indicator occurs in the function. The signal processing unit receives measured values from the airway pressure sensor. Using received measured values of the airway pressure sensor, the signal processing unit generates an airway pressure signal. For a time span at which the patient is not connected to the airway pressure sensor, the signal processing unit uses a predefined value or a value measured before for the airway pressure as a value of the airway pressure signal.

The signal processing unit automatically generates a volume flow signal or a volume signal or both the volume flow signal and the volume signal. The signal processing unit generates the volume flow signal with the use of measured values of a volume flow sensor, wherein the signal processing unit has received these measured values. This volume flow sensor measures an indicator for the volume flow of breathing air to and/or from the patient. The signal processing unit generates the volume signal with the use of measured values of a filling level sensor. This filling level sensor measures an indicator for the filling level of the lungs of the patient.

The signal processing unit carries out at least one of the following three sequences automatically, i.e., the first and/or second and/or third sequence. It is possible that two or all three of these three sequences are carried out.

The first sequence comprises the following steps:

The signal processing unit receives measured values from
at least one breathing sensor. The received measured
values of the breathing sensor pertain to an indicator,
which is correlated with the first pneumatic indicator to
be determined.

Using measured values of the breathing sensor, the signal
processing unit generates the first respiratory signal,
which occurs in the first relationship.

For the model parameter or for each model parameter,
which appears in the first relationship, the signal processing unit derives a respective value. The signal
processing unit uses for the derivation of such a model
parameter the predefined function as well as signals
which appear in this function and which the signal
processing unit has generated with the use of received
measured values.

The signal processing unit determines the first pneumatic
indicator. It uses for this the predefined first relationship as well as the derived value or at least one
respective derived value of the model parameter or
each model parameter, which occurs in the first relationship.

The second sequence comprises the corresponding steps,
but for the second rather than for the first pneumatic indicator, and with the use of the second rather than of the first
predefined relationship.

The third sequence comprises the following steps:

The signal processing unit receives measured values from
at least one breathing sensor. The measured values from
this breathing sensor pertain to an indicator, which
correlates with the overall pneumatic indicator for the
breathing activity of the patient.

Using measured values of the breathing sensor, the signal
processing unit generates the overall respiratory signal,
which occurs in the overall relationship.

The signal processing unit derives a value for the model
parameter or for each model parameter that occurs in
the overall relationship. The signal processing unit uses
for the derivation of such a model parameter value the
predefined function as well as signals that occur in this
function and that have been generated by the signal
processing unit with the use of received measured
values, The signal processing unit determines the overall pneumatic indicator. It uses for this purpose the predefined
overall relationship as well as the derived value or at
least one respective derived value of the model parameter or of each model parameter which occurs in the
overall relationship.

Consequently, the following alternatives are possible
according to the present invention:

1. The first pneumatic indicator and the second pneumatic
indicator are determined (the first sequence and the
second sequence are carried out).

2. The first pneumatic indicator and the overall pneumatic
indicator are determined, but the second pneumatic
indicator is not (the first sequence and the third
sequence are carried out).

3. The second pneumatic indicator and the overall pneumatic indicator are determined, but the first pneumatic
indicator is not (the second sequence and the third
sequence are carried out).

4. The first pneumatic indicator is determined, but neither
the second pneumatic indicator nor the overall pneumatic indicator are determined (only the first sequence is carried out, but neither the second sequence nor the third sequence is carried out).

5. The second pneumatic indicator is determined, but neither the first pneumatic indicator nor the overall pneumatic indicator is carried out (only the second sequence is carried out, but neither the first sequence nor the third sequence is carried out).

6. The overall pneumatic indicator is determined, but neither the first pneumatic indicator nor the second pneumatic indicator are determined (only the third sequence is carried out, but neither the first sequence nor the second sequence is carried out).

No further steps are necessary in the first alternative, because both pneumatic indicators are determined. It is possible in the first alternative that the overall pneumatic indicator is additionally determined (third sequence).

The second pneumatic indicator is determined in the second alternative, and the first pneumatic indicator and the overall pneumatic indicator are used for this.

The first pneumatic indicator is determined in the third alternative, and the second pneumatic indicator and the overall pneumatic indicator are used for this.

The overall pneumatic indicator and then the second pneumatic indicator are determined in the fourth alternative. To determine the overall pneumatic indicator, the signal processing unit uses the already determined first pneumatic indicator as well as at least one of the following pieces of information:

The volume flow signal, which has been generated from measured values of the volume flow sensor, and/or the volume flow signal, which has been generated from measured values of the filling level sensor, and/or a predefined percentage function, which specifies the percentage of the first pneumatic indicator or of the second pneumatic indicator in the overall pneumatic indicator.

The percentage function specifies the percentage of the first region or of the first process in the overall pneumatic indicator. Or else, the percentage function specifies the percentage of the second region or of the second process. Or else, the percentage function specifies the percentage of the second region or of the second process in relation to that of the first region or of the first process.

In order to determine the second pneumatic indicator in the fourth alternative, the signal processing unit uses the previously determined first pneumatic indicator and the overall pneumatic indicator, which is now determined.

The overall pneumatic indicator and then the first pneumatic indicator are determined in a corresponding manner in the fifth alternative, likewise with the use of the volume flow signal and/or of the volume flow signal and/or of the percentage function.

In the sixth alternative, the signal processing unit determines both the first pneumatic indicator and the second pneumatic indicator from the already determined overall pneumatic indicator. The signal processing unit uses for the determination of the two pneumatic indicators the overall pneumatic indicator and in addition the generated volume flow signal and/or the generated volume signal and/or the predefined percentage function.

According to the present invention, a first pneumatic indicator and a second pneumatic indicator for the intrinsic breathing activity of the patient are determined. The first pneumatic indicator describes the activity of a first region of the respiratory system or a first process during the breathing of the patient. The second pneumatic indicator describes the activity of a second region of the respiratory system or a second process during the breathing of the patient. The superimposition of these two pneumatic indicators, in most cases, the sum or weighted sum of these two pneumatic indicators, is a pneumatic indicator for the overall breathing activity of the patient.

Knowledge of these two pneumatic indicators makes it possible, for example, to control a mechanical ventilator in a more specific manner than if only a single pneumatic indicator were known for the overall breathing activity or only one pneumatic indicator were known for a region of the respiratory system. In particular, the ventilator can be controlled depending on only the first pneumatic indicator or on only the second pneumatic indicator. Or else, the two pneumatic indicators are compared with each other in order to control the ventilator. The ventilator controls in this manner supports or trains a region and/or a process in a specific manner during the breathing of the patient.

In one application of the present invention, the auxiliary respiratory muscular system acts as one region and the diaphragmatic muscular system of the patient acts as another region. These two regions together essentially bring about the breathing of the patient. Thanks to the present invention, it can be determined in this application what percentage or absolute value of the overall breathing activity of the patient is currently accounted for by the auxiliary respiratory muscular system. A percentage above a predefined limit or even below another predefined limit may require a change in the controlling of the ventilator. A corresponding message is preferably output in a form perceptible by a person, or the ventilator is automatically controlled correspondingly.

The two pneumatic indicators to be determined cannot, as a rule, be measured directly and especially they cannot be measured separately from one another. The two indicators are rather determined according to the present invention with the use of different measured indicators and signals indirectly, which will be explained below.

In particular while the patient is ventilated mechanically by a mechanical ventilator, a preferably pneumatic indicator for the airway pressure is measured according to the present invention, for example, in a fluid connection between the patient and a measuring device, wherein the measuring device may be a component of the ventilator or may be arranged outside of the ventilator, especially close to the mouth of the patient. This preferably pneumatic indicator is often called $P_{aw}$ (pressure in airway), but it may also be a pneumatic pressure $P_{es}$ (pressure in esophagus) in the esophagus or a gastric pressure $P_{ga}$ in the stomach, which is likewise used as an indicator for the airway pressure. The pressure is preferably measured relative to the ambient pressure. This airway pressure $P_{aw}$, $P_{es}$, $P_{ga}$, which is variable over time, is generated by the respiratory muscular system of the patient (spontaneous breathing) or by a ventilator or by a superimposition of the spontaneous breathing and the mechanical ventilation of the patient.

The process according to the present invention can be used when the patient is not currently being ventilated mechanically; more generally, when the patient is not currently connected to a sensor for the airway pressure $P_{aw}$ or $P_{es}$ or $P_{ga}$. In one application, a preferably constant value, e.g., zero (airway pressure equal to the ambient pressure— this corresponds to the breathing effort of the patient when he is not being ventilated mechanically) is predefined for the airway pressure $P_{aw}$. No sensor is necessary for the airway pressure in this case. The two pneumatic indicators are determined according to the present invention in this case as well.

Furthermore, the volume flow of breathing air into and/or out of the lungs of the patient and/or into and/or out of the airway of the patient is measured according to the present invention, preferably with a pneumatic sensor. This volume flow is likewise measured, for example, in the fluid connection between the patient and the measuring device, preferably close to the mouth of the patient, or at the ventilator. Preferably, a time delay between the measurement point and the airway or the lungs is predefined or determined, and is then taken into consideration. Or else, the time delay may be considered to be negligibly short. As an alternative or in addition to this, the current volume of the lungs is measured, e.g., with a mechanical or optical sensor. The volume can be calculated from the volume flow and conversely, the volume flow can be determined from the volume. Measurement of both signals leads to redundancy.

Two different pneumatic indicators are determined according to the present invention. In one embodiment, the two pneumatic indicators describe the respective activity of two different regions of the respiratory system, which are preferably separated from one another in space, e.g., the activity of the diaphragmatic muscle and the activity of an auxiliary breathing muscle or the activity of a left region of the body and the activity of a right region of the body or the activities in two different groups of muscles, which are responsible for two different functions during breathing. In another embodiment, the two pneumatic indicators describe the respective activity in two different processes, which the patient carries out during breathing, e.g., inhalation (inspiration, first pneumatic indicator) and exhalation (expiration, second pneumatic indicator) or the regular breathing (first pneumatic indicator) with inhalation and exhalation as well as irregular processes, e.g., coughing and sneezing or spasms (second pneumatic indicator). These two processes do not preferably overlap in time.

In one embodiment, a volume flow sensor repeatedly measures the respective current volume flow, and the volume flow sensor is preferably a pneumatic sensor. The signal processing unit generates a volume flow signal from measured values of the volume flow sensor. The signal processing unit generates the volume signal from the volume flow signal by numeric integration. The signal processing unit preferably calculates the current filling level for the lungs of the patient from a plurality of measured values from the volume flow sensor. The signal processing unit preferably calculates the current filling level of the lungs from a plurality of measured values for the volume flow, which pertain to different times, by numerical integration. This configuration eliminates the need to provide a volume sensor.

In another embodiment, a volume sensor repeatedly measures the respective current volume, i.e., the filling level of the lungs. This volume sensor comprises, for example, an image recording device and an image analysis unit or a mechanical sensor, e.g., a wire strain gauge or another position sensor. The signal processing unit generates the volume flow signal from this volume signal by numerical differentiation.

In one embodiment of this configuration, the signal processing unit receives, additionally or instead, measured values from a filling level sensor, which measures an indicator for the current filling level of the lungs of the patient. This filling level sensor may be a pneumatic or electrical or even an optical sensor. For example, an image recording device generates images of the patient, and an image analysis unit analyzes these images, especially by the application of an imaging process, in order to measure the filling level of the lungs.

In an alternative embodiment, the signal processing unit receives both measured values from a volume flow sensor and measured values from a volume sensor. The signal processing unit generates both a volume flow signal and a volume signal. This configuration leads to redundancy and avoids errors, which may otherwise occur, if the volume were calculated from the volume flow signal or if the volume flow were calculated from the volume signal.

In one embodiment of the filling level sensor, a geometry sensor measures an indicator for the body geometry such that this measured body geometry is correlated with the current filling level of the lungs. For example, the geometry sensor measures the current body circumference or the position or the movement or the acceleration of a measuring body on the skin of the patient by means of a transducer, which is positioned on the skin of the patient close to the lungs and is moved depending on the filling level of the lungs. The transducer changes its position depending on the filling level of the lungs. It is also possible that an image recording device and an imaging process are used in order to measure the value for the body geometry.

It is also possible to determine an indicator for the filling level of the lungs indirectly from the measured values of the volume flow sensor, on the one hand, and to measure it directly by means of the filling level sensor, on the other hand.

According to the invention, two relationships between the two pneumatic indicators and the respiratory signals are predefined. Or else, an overall relationship between the overall pneumatic indicator and the overall respiratory signal is predefined. At least one of these three relationships has at least one model parameter, and optionally each relationship does. The respective value of the model parameter or of each model parameter in the relationships is, as a rule, unknown in advance. According to the invention, the signal processing unit derives at least once a respective value for the model parameter or for each model parameter and optionally a plurality of values for the same model parameter one after another. The signal processing unit uses different signals for this derivation.

In one embodiment, the signal processing unit combines a plurality of measured values into one signal, for example, by smoothing or by forming a mean value or a median. For example, the signal processing unit combines all measured values from the breathing sensor, which the breathing sensor has measured in the course of a phase of a breath, into a signal value of the first or second pneumatic signal or of the overall pneumatic signal. This one phase is, for example, the inhalation (inspiration) or the exhalation (expiration) during a breath.

According to the present invention, a function is predefined, which describes an indicator for the airway pressure as a function of the volume flow and/or of the filling level of the lungs as well as of the two pneumatic indicators or of the overall pneumatic indicator. In one embodiment, this function has the following form:

$$P_{aw}(t)=f0[\text{Vol}'(t),\text{Vol}(t)]+P_{mus,1}(t)+P_{mus,2}(t)+\text{Res}_{ges}(t)$$

or $$P_{es}(t)=f0[\text{Vol}'(t),\text{Vol}(t)]+P_{mus,1}(t)+P_{mus,2}(t)+\text{Res}_{ges}(t),$$

wherein $$P_{mus,1}(t)=f1[Sig_1(t),Vol'(t),Vol(t),w_1(t)]$$

and $$P_{mus,2}(t)=f2[Sig_2(t),Vol'(t),Vol(t),w_2(t)].[ges=overall]$$

Here, f0, f1, f2 are transfer functions, which may be nonlinear. Vol' is the volume flow into and out of the lungs of the patient, which is variable over time; Vol is the filling level of the lungs, which is variable over time, $Sig_1$ is the first respiratory signal and $Sig_2$ is the second respiratory signal. The functions f0, f1 and f2 are predefined. The function f0 does not depend on a respiratory signal, the function f1 depends on the first respiratory signal $Sig_1$ and the function f2 depends on the second respiratory signal $Sig_2$. In one embodiment, both f1 and f2 have each at least one model parameter. The function f0 optionally also has at least one model parameter. The terms $w_1(t)$ and $w_2(t)$ are random noise terms. The summand $Res_{ges}$ (overall residuum) describes the noise, which is variable over time, based on measurement errors and/or process errors (deviations between the model and reality).

If generally N respiratory signals can be measured, at least N pneumatic indicators can be distinguished and determined, and the function has the following form:

$$P_{aw}(t)=f0[Vol'(t),Vol(t)]+f1[Sig_1(t),Vol'(t),$$
$$Vol(t),w_1(t)]+ \quad . \quad . \quad . \quad +fN[Sig_N(t),Vol'(t),$$
$$Vol(t),w_N(t)]+Res_{ges}(t)$$

or $$P_{es}(t)=f0[Vol'(t),Vol(t)]+f1[Sig_1(t),Vol'(t),$$
$$Vol(t),w_1(t)]+ \quad . \quad . \quad . \quad +fN[Sig_N(t),Vol'(t),$$
$$Vol(t),w_N(t)]+Res_{ges}(t).$$

The contributions or percentages of at least N regions or processes to the overall breathing activity can therefore generally be determined. According to this embodiment, N relationships are predefined each between a respective pneumatic indicator each and a respective measurable respiratory signal, and at least one and preferably each relationship has at least one respective model parameter.

The case in which two pneumatic indicators $P_{mus,1}$ and $P_{mus,2}$ are determined and two relationships are predefined will be described again below.

In one embodiment, the signal processing unit applies at least one statistical method to the predefined function and/or to the two relationships and/or in the calculation of a signal from the measured values and/or in the derivation of a model parameter value. By applying this statistical method, random measured values, freak values, as well as the influence of noise can be compensated to a certain degree. In addition, it is possible in many cases to calculate an assessment on the reliability that a determined pneumatic indicator agrees with the corresponding actual pneumatic indicator.

In one embodiment, the signal processing unit applies a regression method to generate a signal from the measured values and/or to determine a pneumatic indicator from at least one respiratory signal and/or to derive a model parameter value. This embodiment makes it possible to additionally calculate an empirical variance or dispersion and to use it as a value for the reliability. In another embodiment, the signal processing unit applies a machine learning method, and it trains, for example, a neuronal network. The measured airway pressure may be a pressure outside of the patient, for example, the pressure in airway ($P_{aw}$) or air pressure in front of the mouth, or it may occur within the patient, e.g., a pressure $P_{es}$ in the esophagus.

If the ventilator controls the mechanical ventilation as a function of pressure (pressure-controlled ventilation, a desired time course of the pressure is the command variable), the ventilator imposes the airway pressure $P_{aw}(t)$ as the pressure source of the ventilation, i.e., it controls the ventilation pressure generated by the ventilation with the control gain of the closed-loop control that the superimposition of the spontaneous breathing of the patient and the ventilation air pressure generated by the ventilator is equal to a predefined airway pressure. The volume flow Vol'(t) and the filling level of the lungs Vol(t) become established such that the equation shown above is satisfied. If the ventilator controls the mechanical ventilation as a function of the volume (volume-controlled ventilation, a desired time process of the volume is the command variable), the airway pressure $P_{aw}(t)$ becomes established depending on the ventilation.

In an alternative of the present invention, the signal processing unit receives measured values from at least one ventilation sensor and from other sensors, and generates from the measured values received the two respiratory signals. Different embodiments are possible concerning the manner in which the signal processing unit generates the two respiratory signals with the use of the measured values of the breathing sensor or of a plurality of breathing sensors. The embodiments also apply correspondingly to the other alternatives of the present invention.

In one embodiment, the signal processing unit receives measured values from two breathing sensors, preferably from two sets of breathing sensors, e.g., from two sets of measuring electrodes, which are positioned in two different regions, located at spaced locations from one another, on the skin of the patient. The signal processing unit generates the two respiratory signals from the measured values.

In a variant of this embodiment, the fact is used that an overall respiratory signal Sig can be generated, which is correlated with the overall intrinsic breathing activity of the patient, for example, while the ventilator does not ventilate the patient at all or it ventilates him in a open-loop control rather than closed-loop control manner. The overall respiratory signal Sig is correlated with the overall pneumatic indicator $P_{mus}$. An additional function is predefined in a computer-accessible form. This additional function describes an overall pneumatic indicator $P_{mus}$ as a function of the first pneumatic indicator $P_{mus,1}$ and of the second pneumatic indicator $P_{mus,2}$, In particular, the overall pneumatic indicator $P_{mus}$ is the sum of the first and second pneumatic indicators. The signal processing unit generates the overall respiratory signal Sig, which is correlated with the overall pneumatic indicator $P_{mus}$ For example, the airway pressure sensor measures the pneumatic pressure $P_{es}$ in the esophagus and uses the measured pressure $P_{es}$ to generate the overall respiratory signal Sig.

The predefined function Fkt, the predefined additional function and the two predefined relationships $Zus_1$, $Zus_2$ are used. As was just described, an overall respiratory signal $P_{mus}$ is generated; in addition, the two respiratory signals, which are correlated with the two pneumatic indicators $P_{mus,1}$ and $P_{mus,2}$, are generated. Each model parameter value in the relationships and optionally in the functions is derived approximately, and an overdetermined system of equations is used in some cases. As a result, the two pneumatic indicators are determined with a higher certainty.

The signal processing unit generates the overall respiratory signal and uses for this generation measured values from the airway pressure sensor as well as from the volume flow sensor and/or from the volume sensor. In addition, the signal processing unit determines the overall pneumatic indicator $P_{mus}$. The signal processing unit additionally uses the additional function as well as the overall respiratory signal Sig to derive the two respiratory signals $Sig_1$, $Sig_2$ and, with the use of these signals, the model parameter value or at least one model parameter value. Using this model parameter value and the overall pneumatic indicator $P_{mus}$, the signal processing unit determines the two pneumatic indicators $P_{mus,1}$, $P_{mus,2}$. It preferably uses for this additionally the two respiratory signals $Sig_1$, $Sig_2$, which have been generated, e.g., by means of measured values from at least two breathing sensors.

The necessity to use two different sets of breathing sensors is avoided in different alternative embodiments. One set of sensors is sufficient. Given prior knowledge is used, instead, in an alternative embodiment. Additional signals are used in other alternative embodiments to determine the two pneumatic indicators from an overall pneumatic indicator or from an overall respiratory signal.

According to the present invention, the signal processing unit generates a volume flow signal and/or a volume signal from corresponding measured values. In an alternative embodiment, the signal processing unit generates the first pneumatic indicator and the second pneumatic indicator from the overall pneumatic indicator determined in advance and additionally from the volume flow signals and/or from the volume signal. This alternative embodiment also eliminates the need to use an additional sensor, and it uses prior knowledge, which can be derived from the volume flow signal and/or from the volume signal or is predefined. It is also possible to generate first an overall respiratory signal, preferably from measured values of at least one breathing signal. The signal processing unit generates from this overall respiratory signal the two respiratory signals with the use of the prior knowledge. Using these two respiratory signals and the predefined first and second relationships, the signal processing unit determines the two pneumatic indicators $P_{mus,1}$, $P_{mus,2}$.

In one embodiment, a percentage function p1 or p2 is predefined, wherein p1(t) describes the percentage of the first region or of the first process as a function of the time t during an individual breathing process, i.e., during a single-time inhalation and exhalation, and p2(t) describes the percentage of the second region or second process in the overall breathing activity of the patient. Now, $P_{mus,1}(t)=$ P1(t)*$P_{mus}$(t) and $P_{mus,2}$(t)=p2(t)*$P_{mus}$(t) as well as preferably $P_{mus}$(t)=$P_{mus,1}$(t)+$P_{mus,2}$(t). Consequently, both pneumatic indicators $P_{mus,1}$ and $P_{mus,2}$ can be determined from an overall pneumatic indicator $P_{mus}$ as well as from the predefined percentage function p1 or p2. It is also possible to determine first the first pneumatic indicator $P_{mus,1}$ with the use of the first respiratory signal $Sig_1$ or the second pneumatic indicator $P_{mus,2}$ with the use of the second respiratory signal $Sig_2$. Using the predefined percentage function p1 or p2, the overall pneumatic indicator $P_{mus}$ as well as the second pneumatic indicator $P_{mus,2}$ are determined from the first pneumatic indicator $P_{mus,1}$ and the overall pneumatic indicator and the first pneumatic $P_{mus,1}$, indicator are determined from the second pneumatic indicator $P_{mus,2}$.

An overall respiratory signal Sig is optionally determined, and the signal processing unit generates from this overall signal the two respiratory signals $Sig_1$, $Sig_2$ with the use of the percentage function. The signal processing unit then determines the two pneumatic indicators from the two respiratory signals.

In a special form of this embodiment, the first region is the part of the breathing muscular system, which part is used for inhalation, and the second region is the region used for exhalation. It can be postulated in many cases that $P_{mus,2}$(t)=0 during inhalation and $P_{mus,1}$(t)=0 during exhalation. To determine the two pneumatic indicators $P_{mus,1}$, $P_{mus,2}$, it is determined when the patient is inhaling and when he is exhaling, wherein inhalation and exhalation may be elicited by the spontaneous breathing and/or by the mechanical ventilation.

In another special form, the signal processing unit detects the respective start and the respective end of at least one breathing process, which the patient carries out. The signal processing unit especially preferably detects the respective start and the respective end of each breathing process. The signal processing unit uses a predefined function as the percentage function. This predefined function specifies the percentage of the overall pneumatic indicator for the first region or for the first process for a plurality of time points during a breathing process. Or else, the predefined function specifies the percentage of the overall pneumatic indicator for the second region or for the second process for a plurality of time points. The inhalation process is preferably standardized to a predefined scale.

These embodiments may be combined. It is possible that the signal processing unit receives measured values from two breathing sensors and additionally uses the percentage function. The combination leads to a deliberate redundancy. In addition, it is more possible in many cases to assess the reliability for the derivation of the model parameter values. Possibly incorrect freak values in the measured values or in the signals can be detected and compensated by calculation more easily.

In one embodiment, a function and first and second relationships are predefined, which are linear at least in the model parameters, for example, as follows:

$$P_{aw}(t)=R*\text{Vol}'(t)+E*\text{Vol}(t)+P_{mus,1}(t)+P_{mus,2}(t)+\text{const}+\text{Res}_{Fkt}(t),$$

$$P_{mus,1}(t)=k_1*Sig_1(t)+w_1(t)$$

and $$P_{mus,2}(t)=k_2*Sig_2(t)+w_2(t)$$

The summand $\text{Res}_{Fkt}(t)$ describes a process noise in the function, and the summands $w_1(t)$ and $w_2(t)$ describe a respective noise in the two relationships.

Instead of $P_{aw}(t)$, it is also possible to use the esophageal pressure $P_{es}(t)$. The linear function has, for example, the following form in this case:

$$P_{es}(t)=E_{cw}*\text{Vol}(t)-P_{mus,1}(t)-P_{mus,2}(t)+\text{const}+\text{Res}_{Fkt}(t).$$

Here, $P_{mus,1}(t)$ and $P_{mus,2}(t)$ are the first pneumatic indicator and the second pneumatic indicator, which describe the activity of the first region of the respiratory system, especially that of the diaphragmatic muscular system, or that of the first process during breathing or the activity of the second region of the respiratory system, especially that of the accessory respiratory muscular system, e.g., of the intercostal muscular system, or that of the second process during the breathing of the patient. The sum $P_{mus}$(t)= $P_{mus,1}$(t)+$P_{mus,2}$(t) is the preferably pneumatic indicator for the overall intrinsic breathing activity of the patient. The two pneumatic indicators $P_{mus,1}$(t) and $P_{mus,2}$(t) are determined according to the present invention.

The predefined lung mechanical model equations comprise a plurality of model parameters. The factor $E_{cw}$ describes the elasticity based on the chest wall (chestwall) of the patient. The factor R describes the breathing resistance, with which the airway of the patient opposes the volume flow. The factor E describes the elasticity of the lungs. The values for the two factors R and E are known and used in one embodiment from earlier measurements. In another embodiment, the factors R and E are model parameters not known in advance, and the signal processing unit derives values for these two factors by applying the statistical method. The factors R and E have a physical meaning each as lung mechanical values, and the calculated values are outputted in one embodiment, especially visually, in a form perceptible by a person.

The summand const results, for example, from the iPEEP (intrinsic positive end-expiratory pressure), i.e., an indicator especially for the effect of an incomplete exhalation by the patient, and it can be measured, e.g., with a probe in the esophagus. Especially when the patient is inhaling completely but exerts only a low intrinsic breathing activity, but he is ventilated mechanically, the influence of iPEEP can in many cases be neglected. The factors R and E as well as the summand const are preferably model parameters. The proportionality factors $k_1$ and $k_2$ are additional model parameters, whose unit is preferably mbar/μV.

Especially if the two respiratory signals are electrical signals, the two proportionality factors $k_1$ and $k_2$ describe each a neuromechanical efficiency of the respiratory system of the patient. The respiratory signals $Sig_1$ and $Sig_2$ describe the electrical impulses, which the body of the patient generates in order to actuate the first region and the second region and to trigger the first process and the second process. These electrical impulses elicit pneumatic processes, which are described by the first and second pneumatic indicators $P_{mus,1}$ and $P_{mus,2}$, respectively. The neuromechanical efficiency describes how well the electrical impulses are converted into pneumatically active activities.

In one embodiment the function and the first and second relationships depend linearly on the model parameters. The function and the first and second relationships also do not necessarily depend linearly on the signals. It is possible in this embodiment to derive the model parameter values by means of a recursive filter, for example, a recursive least-squares filter (RLS). If a recursive filter is used, the estimated values for the model parameters are continuously adapted to the current signal values. In particular, the model parameter values are adapted rapidly to a changing property of the patient, for example, when the patient is changing his posture. The computing time needed. is shorter than when the model parameter values would be calculated anew from zero after each measurement. In addition, better results are often obtained by means of a recursive filter, especially because a fitted curve is not drawn through the measurement points, which would be the case, for example, in case of an interpolation by means of polynomials or splines.

As was already described, an additional function, for example, the function $$P_{mus}(t)=P_{mus,1}(t)+P_{mus,2}(t)$$

is predefined in one embodiment for an overall pneumatic indicator $P_{mus}$.

It is also possible that the influence of a third region or third process on the overall pneumatic indicator is taken into consideration or estimated.

If the first and second relationships are linear at least in the model parameters, the following function, $$P_{mus}(t)=k_1*Sig_1(t)+k_2*Sig_2(t),$$

which is used by the signal processing unit, follows from this.

The esophageal pressure $P_{es}$ (esophagus) is measured in one embodiment, for example, by means of a pneumatic probe in the esophagus of the patient. The signal processing unit generates from the esophageal pressure $P_{es}$ and optionally from the volume flow Vol' an overall respiratory signal Sig, which is correlated with the overall pneumatic indicator $P_{mus}$.

The signal processing unit automatically derives according to the present invention a respective value for the model parameter or for each model parameter in the relationships and optionally in the function and uses it for the derivation of the signals.

In one embodiment, all model parameters are considered to be constant over time. In another embodiment, the possibility that at least one model parameter, preferably each model parameter, may be variable over time is taken into consideration. The respective value of a model parameter is derived in this other embodiment, for example, by smoothing by means of a sliding time window, and only the last N signal values or N signal value sets for the measurable indicators are used for deriving a model parameter value. Here, N is a predefined number. It is also possible to provide each signal value or signal value set or even the last N signal values or N signal value sets with a weighting factor, which is variable over time, and the older the signal value or signal value set is, the lower is the weighting factor.

A function, which is obtained after the time t by a derivation over time of the above-mentioned predefined function, which is linear at least in the model parameters, i.e., for example, the following function obtained by derivation, $$P_{aw}'(t)=R*Vol''(t)+E*Vol'(t)+P_{mus,1}'(t)+\\P_{mus,2}'(t)=R*Vol''(t)+E*Vol'(t)+k_1*Sig_1'(t)+\\k_2*Sig_2'(t),$$

is used as the predefined function in one embodiment.

The constant const does not occur any longer in this function. Signals for the volume flow Vol' and/or the first derivation Vol'' of the volume flow Vol' as well as for the respective first derivation $Sig_1'(t)$ and $Sig_2'(t)$ of the two pneumatic signals are generated from the measured values.

This approach can be applied for a linear function and in some cases also for a non-linear function, which describes the airway pressure as a function of the volume flow and/or of the volume and of the two pneumatic indicators (differencing). This method leads in some cases to a more reliable estimation of the model parameter values.

Both the predefined function and the predefined first and second relationships comply, as a rule, only approximately with reality. In one embodiment, three deviations $Res_{Fkt}(t)$, $Res_1(t)$ and $Res_2(t)$, which vary over time, are taken into consideration, wherein $$Res_{Fkt}(t)=P_{aw}(t)-R*Vol'(t)-E*Vol(t)-P_{mus,1}(t)-\\P_{mus,2}(t)-const,$$

$$Res_1(t)=P_{mus,1}(t)-k_1*Sig_1(t) \text{ and}$$

$$Res_2(t)=P_{mus,2}(t)-k_2*Sig_2(t).$$

After introduction of the first and second relationships, this yields an overall deviation $$\text{Res}_{ges}(t)=P_{aw}(t)-R^*\text{Vol}'(t)-E^*\text{Vol}(t)-k_1^*\text{Sig}_1(t)-k_2^*\text{Sig}_2(t)-\text{const}$$

or also $$\text{Res}_{ges}(t)=P_{aw}'(t)-R^*\text{Vol}'(t)-E^*\text{Vol}'(t)-P_{mus,1}'(t)-P_{mus,2}'(t).$$

In one embodiment, the signal processing unit calculates by means of a statistical method an assessment for the reliability, with which signals are generated from the measured values and/or the two pneumatic indicators $P_{mus,1}(t)$ and $P_{mus,2}(t)$ are determined from the signals, from the function and from the first and second relationships. For example, the signal processing unit carries out a regression analysis and analyzes the empirical variance. Or else, at least one deviation $\text{Res}_{Kfi}(t)$, $\text{Res}_1(t)$, $\text{Res}_2(t)$, $\text{Res}_{ges}(t)$ is treated as a random variable with a predefined distribution, e.g., with a normal distribution, with at least one sought distribution value as with a model parameter. Signals are generated from the measured values, and a random sample is generated from the signals, and the model parameter value or each model parameter value of the probability distribution is derived by means of this random sample. The derived value is used to calculate an analysis of the reliability, e.g., a confidence interval.

The signal processing unit determines in one embodiment which measured values of the sensors have been measured, while the patient is inhaling (inhalation) and which measured values were measuring during the exhalation by the patient (expiration). The signal processing unit splits up the overall respiratory signal or the two respiratory signals into a respective inhalation signal component and an exhalation signal component. In one embodiment, the same function and the same relationships are used for both inhalation and exhalation. At least one model parameter can assume different values for inhalation and exhalation, even in the case of the same function and with the same relationships. A first value which is valid for the inhalation, and a second value which is valid for the exhalation are derived for at least one model parameter in one embodiment. In order to derive a parameter value, which is valid for the inhalation, the signal processing unit uses the measured value or at least some measured values measured during the inhalation, i.e., the inhalation signal component. It avoids the measured values or some measured values measured during the exhalations in order to derive a parameter value for the exhalation, i.e., the exhalation signal component. This configuration leads in many applications to a higher accuracy and/or reliability than when only a single value were derived for each model parameter.

A respective inhalation value and an exhalation value are calculated for each model parameter in one embodiment. This increases the accuracy. An inhalation value and an exhalation value are calculated for individual model parameters only in another embodiment, while only one respective value, which is valid for both the inhalation and the exhalation, is calculated for other model parameters.

For example, the function $$R_{aw}(t)=R^*\text{Vol}'(t)+E^*\text{Vol}(t)+P_{mus,1}(t)+P_{mus,2}(t)+\text{const}$$

is used. An inhalation value and an exhalation value each per sampling time are calculated for the two model parameters R and E. Only a single value per sampling time is calculated for the other model parameters in this function as well as for the model parameters in the relationships.

It is possible in some cases to determine in this manner both respiratory signals and/or both pneumatic indicators from the overall pneumatic indicator or from the overall respiratory signal, especially when the first process is the inhalation and the second process is the exhalation. The signal processing unit receives measured values according to the present invention from different sensors and generates the two respiratory signals and/or the overall respiratory signal as well as the volume flow signal and/or the volume signal. The signal processing unit preferably processes the received measured values in order to generate the signals. Especially in the case of electrical breathing sensors, the signal processing unit generates at least one measured value series, compensates the influence of interference signals by calculation at least approximately, and calculates a so-called enveloping curve (envelope), which is formed due to the absolute value being formed from each measured value, and each derived measured value series thus formed is smoothed. The result of the respective preprocessing is used as a signal in the sense of the claims.

In one embodiment, the signal processing unit triggers the step of outputting the first pneumatic indicator and/or the second pneumatic indicator and/or the overall pneumatic indicator and/or a variable derived from the two pneumatic indicators in a form perceptible by a person, for example, displayed on an output device. For example, the time curve of the two pneumatic indicators is displayed.

In one embodiment, the signal processing unit detects the start and the end of at least one breathing process, preferably the start and the end of each breathing process within a test period. Each breathing process comprises exactly one inhalation process (inhalation) and exactly one exhalation process (exhalation). The signal processing unit calculates for each detected breathing process at least one of the following variables depending on the two pneumatic indicators determined according to the present invention:

The ratio of the first pneumatic indicator to the second pneumatic indicator during a breathing process, for example, the quotient of the maximum of the first pneumatic indicator and the maximum of the second pneumatic indicator in the course of the breathing process, the phase difference (phase shift) between the first pneumatic indicator and the second pneumatic indicator, cf. explanation below, the neuromechanical efficiency for the first regions or for the first process, i.e., the ratio of the first pneumatic indicator to the first respiratory signal, and the neuromechanical efficiency for the second region or for the second process, i.e., the ratio of the second pneumatic indicator to the second respiratory signal.

The neuromechanical efficiency indicates how well an electrical respiratory signal is converted in the body of the patient into a pneumatically measurable activity of the respiratory muscle.

The embodiment with the phase shift will be explained below. Breathing is a periodic process, and a full breath is an individual period. The breaths are standardized, for example, on a scale of 0° to 360° or 0° to 2*Π. It is then determined at which time (phase) on this standardized scale the first pneumatic indicator $P_{mus,1}$ as well as the second pneumatic indicator $P_{mus,2}$ exceed a predefined threshold value and thus become "active". An example: If the first pneumatic indicator $P_{mus,1}$ describes the activity during inhalation and the second pneumatic indicator $P_{mus,2}$ describes the activity during exhalation, the first pneumatic indicator $P_{mus,1}$ has a phase that is, for example, between 0° and 30°, and the second pneumatic indicator $P_{mus,2}$ usually has a phase that is greater than 100°, especially greater than 150°. The deviation between these two phases is called the phase difference or also phase shift.

In one application of the present invention, a ventilator supports the breathing activity of the patient. The ventilator performs a plurality of ventilation strokes one after another during this support, i.e., during this mechanical ventilation.

The ventilation strokes or at least some ventilation strokes are triggered in one embodiment of this application automatically depending on the determined first pneumatic indicator $P_{mus,1}$ and/or depending on the determined second pneumatic indicator $P_{mus,2}$.

In another embodiment of this application, the signal processing unit calculates the percentage or contribution of the breathing activity of the patient P to the first region/process and/or to the second region/process. The signal processing unit uses for this calculation the two determined pneumatic indicators $P_{mus,1}$ and $P_{mus,2}$. If the calculated percentage is above or below a predefined limit, the signal processing unit triggers at least one of the following two steps:

A message is outputted, preferably in a form perceptible for a person. This message comprises information on the calculated percentage.

The ventilator is actuated automatically with the aim of changing the percentage.

In a variant of this additional embodiment, the signal processing unit repeatedly determines the two pneumatic indicators $P_{mus,1}$ and $P_{mus,2}$. The signal processing unit carries out at least one of the following two steps:

It checks whether a percentage of the overall breathing activity, which percentage is above a predefined limit, is changing to and fro between the first region/process and the second region/process, and it checks whether a time shift, which is above a predefined limit, occurs between the time curves of the breathing activity of the first region/process and of the second region/process, e.g., if the above-mentioned phase shift is present.

If one of these two events is detected, the signal processing unit triggers at least one of the following steps:

A message is outputted or the ventilator is actuated with the aim of changing the percentage or the time shift.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

Figure 1:
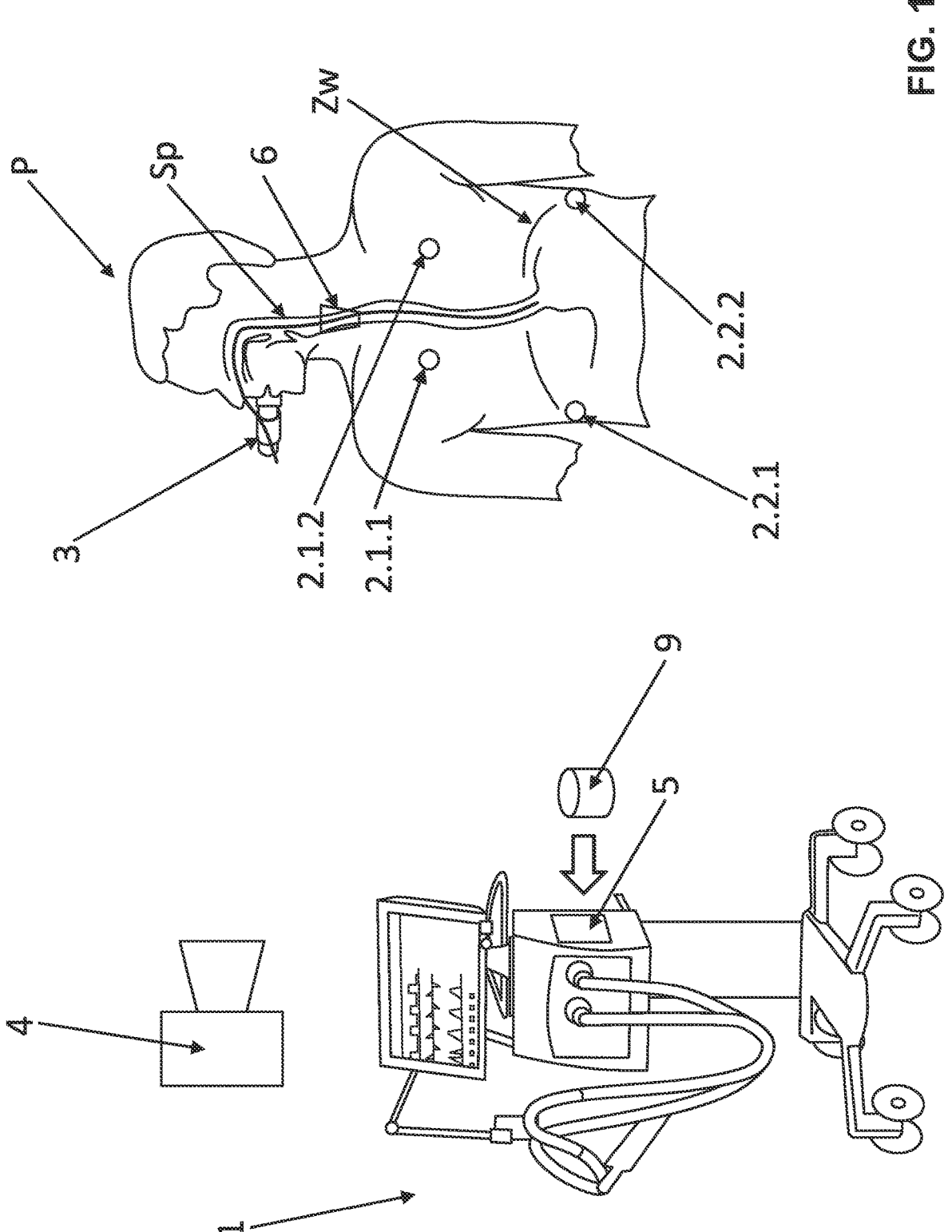
FIG. 1 schematically shows which sensors measure different indicators, which are used for the determination of the two pneumatic indicators.

DESCRIPTION OF PREFERRED
EMBODIMENTS

Referring to the drawings, values for two pneumatic indicators $P_{mus,1}$ and $P_{mus,2}$, which are variable over time and which describe the breathing activity of a first region or of a second region of a patient P, while the patient P is ventilated mechanically by a ventilator at least from time to time, shall be continually determined in the exemplary embodiment. The first region is the muscles of the diaphragm, and the second region is a breathing muscle in a first application. The first region is the breathing muscle of the left half of the body and the second region is the breathing muscle of the right half of the body in a second application. In a third application, the first pneumatic indicator $P_{mus,1}$ describes the inhalation (inspiration) and the second pneumatic indicator $P_{mus,2}$ describes the exhalation (expiration) by the patient P, i.e., two different processes.

FIG. 1 schematically shows which signals are measured. Shown are

The patient P, the esophagus Sp and the diaphragm Zw of the patient P, a ventilator 1, which ventilates the patient mechanically at least from time to time, and comprises a data-processing signal processing unit 5, which has reading access to a memory 9 at least from time to time, four sets 2.1.1 through 2.2.2 of sensors with at least one measuring electrode each, wherein the measuring electrode sets 2.1.1 and 2.1.2 are arranged parallel to the sternum, and the measuring electrode sets 2.2.1 and 2.2.2 are arranged at the costal arch, a pneumatic sensor 3, which measures the airway pressure $P_{aw}$ in front of the mouth of the patient P, an optional sensor 4, which comprises an image recording device and an image analysis unit, and is directed towards the thoracic region of the patient P, and an optional pneumatic sensor 6 in the form of a probe in the esophagus Sp of the patient P.

Figure 2:
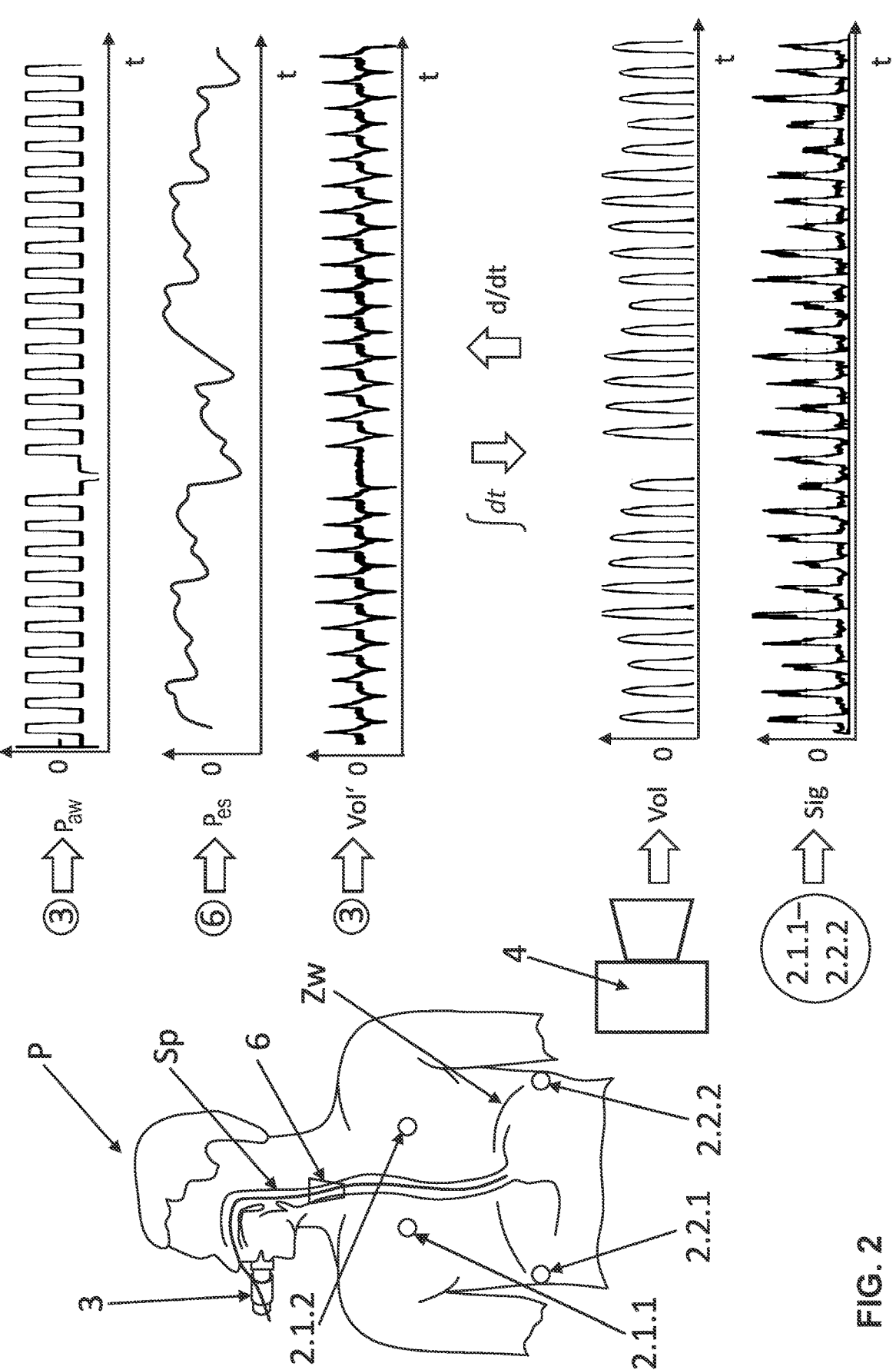
FIG. 2 shows which signals are derived from the measured values of which sensors.

FIG. 2 shows the signals that are generated with the use of the measured values of these sensors.

The four measuring electrode sets 2.1.1 through 2.2.2 of measuring electrodes provide two electrical respiratory signals $Sig_1$ and $Sig_2$, which are correlated with the first pneumatic indicator $P_{mus,1}$ and with the second pneumatic indicator $P_{mus,2}$, respectively. At the time of the first application, the two measuring electrode sets 2.2.1 and 2.2.2 provide the measured values for the first respiratory signal $\text{Sig}_1$, which is correlated with the activity of the diaphragmatic muscles, and the two measuring electrode sets 2.1.1 and 2.1.2 provide the measured values for the second respiratory signal $\text{Sig}_2$, which is correlated with the activity of the auxiliary breathing muscle (intercostal muscle). At the time of the second application, the two measuring electrode sets 2.1.1 and 2.2.1 provide the measured values for the first respiratory signal $\text{Sig}_1$, which is correlated with the activity of the breathing muscle of the right half of the body, and the two measuring electrode sets 2.1.2 and 2.2.2 provide the measured values for the second respiratory signal $\text{Sig}_2$, which is correlated with the activity of the breathing muscle of the left half of the body.

Instead of measuring electrodes 2.1.1 through 2.2.2, it is also possible to use at least two sets of mechanomyogram sensors, which yield measured values for the two pneumatic signals $\text{Sig}_1$ and $\text{Sig}_2$.

The overall breathing activity $P_{mus}$ of the patient P is formed in the example shown due to a superimposition of these regions and hence of these pneumatic indicators $P_{mus,1}$ and $P_{mus,2}$, i.e., $$P_{mus}(t)=P_{mus,1}(t)+P_{mus,2}(t) \tag{1}$$

holds true at each time t.

It is also possible to generate three or more than three respiratory signals with a correspondingly larger number of sensors for three or more different regions of the breathing muscle of the patient P, or for three or more processes during the breathing.

The pneumatic sensor 3 provides measured values, from which the airway pressure $P_{aw}$ (pressure in airway) in front of the mouth of the patient P is derived. This airway pressure $P_{aw}$ is preferably the difference from the ambient pressure, and it is formed from a superimposition of the intrinsic breathing activity of the patient P, described by $P_{mus}$, and the mechanical ventilation by the ventilator 1. During time periods during which the patient P is not ventilated mechanically, the airway pressure $P_{aw}$, which is derived from measured values of the sensor 3, arises exclusively from the intrinsic breathing activity (spontaneous breathing) of the patient P. The optional probe 6 provides measured values, from which the esophageal pressure $P_{es}$ (pressure in esophagus) is derived.

In addition, a signal Vol', which is variable over time, is generated, which is correlated with the flow rate, i.e., with the volume of air per unit of time, which flows into or out of the lungs of the patient P. This signal Vol' is likewise generated by means of measured values of the sensor 3 or by means of measured values of another sensor. A signal Vol, which is correlated with the current filling level Vol of the lungs of the patient P, is calculated from the signal Vol' by numeric integration over time.

In one embodiment, the image recording device of the sensor 4 generates images of the thoracic region of the patient P continually. These images show the geometry of the thoracic region. This geometry is correlated with the current filling level of the lungs Vol. The image analysis unit analyzes the images of the thoracic region and derives the signal Vol from them. The signal Vol' for the flow rate is derived from the signal Vol for the current filling level of the lungs, especially by numeric differentiation.

The two embodiments, namely, the one in which the sensor 3 or an additional sensor measures the signal Vol' for the flow rate and the signal Vol for the filling level of the lungs is derived, and the one in which the sensor 4 measures the signal Vol for the filling level of the lungs and the signal for the flow rate Vol' is derived, may be combined with one another in order to generate more reliable signals Vol and Vol' and/or to deliberately bring about redundancy.

Figure 3:
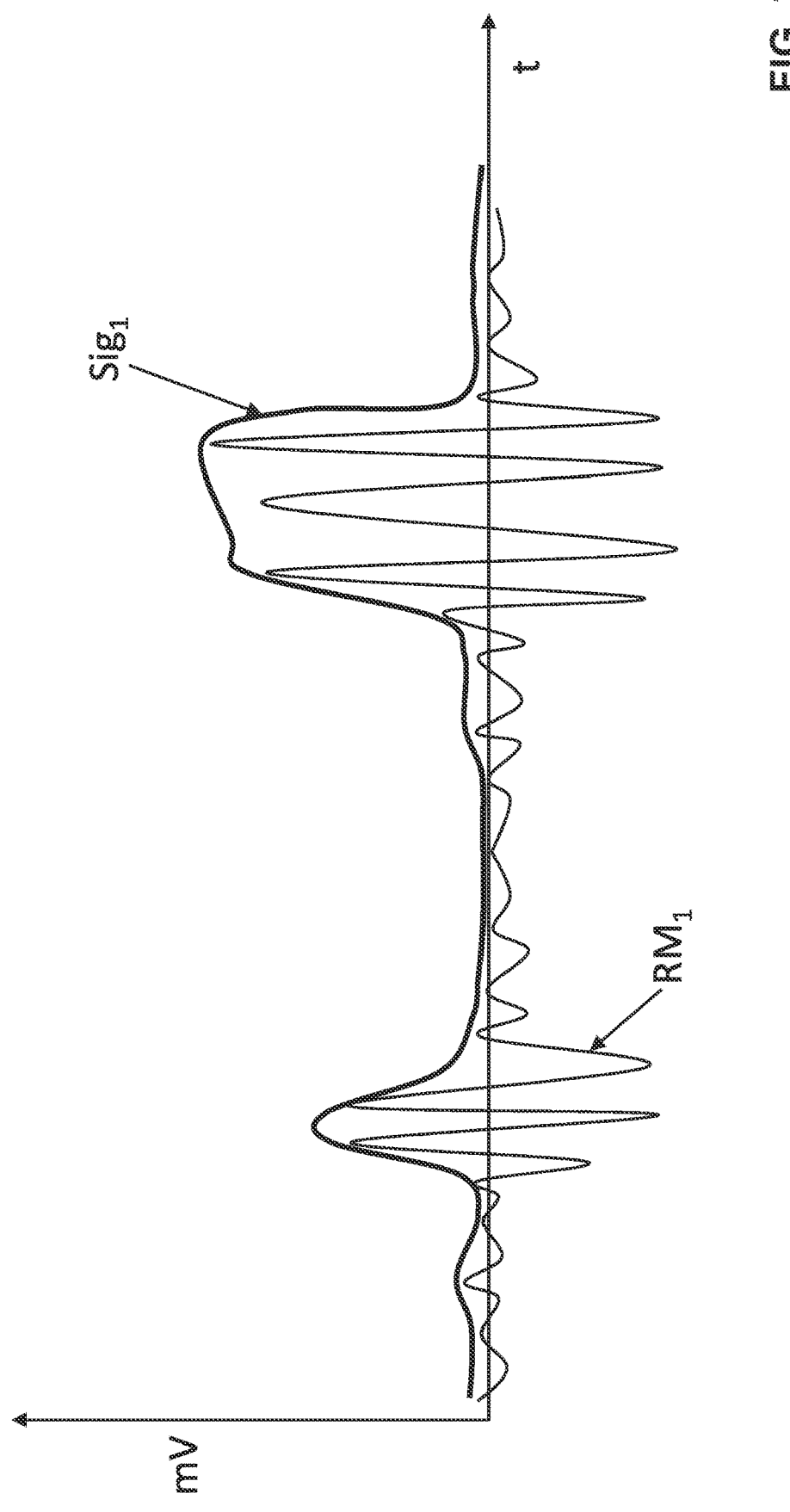
FIG. 3 shows as an example how a signal is obtained by signal processing from the raw measured values of sensors.

FIG. 3 shows in an example how the signal processing unit 5 generates a signal from the raw measured values. The time curve RM of the raw measured values of a set of measuring electrodes as well as the signal $\text{Sig}_1$ are shown as an example. The raw measured values RM are calculated by noise and interferences being suppressed in the voltages, which are provided by the measuring electrode sets 2.1.1 through 2.2.2, and by the influence of signals of the cardiac muscles (ECG signal) being compensated at least approximately by calculation. The signal $\text{Sig}_1$ is obtained by smoothing the time curve of the raw measured values RM. A so-called enveloping curve (envelope) is calculated from the raw measured values RM in the example shown and is used as the signal $\text{Sig}_1$. This enveloping curve is generated by linear or nonlinear smoothing over the maxima of the values of the raw measured values RM in a respective predefined time period and it has only positive signal values.

Figure 4:
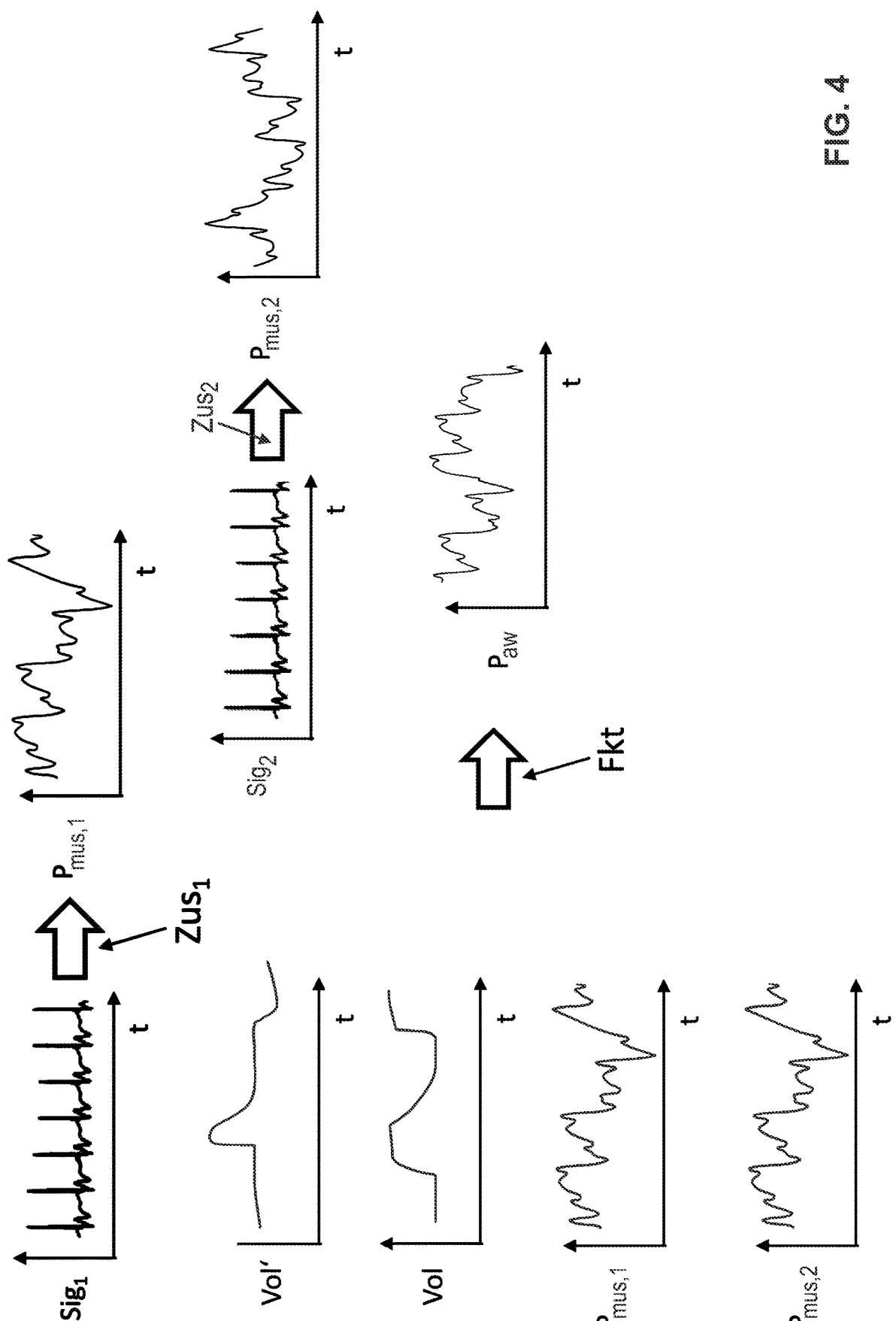
FIG. 4 schematically shows which pneumatic indicators are derived from the signals generated with the use of which functions and of which relationships.

FIG. 4 schematically shows an embodiment showing which pneumatic indicators are derived from the measured signals and which functions and relationships are used. The term "function" will be used below to describe the dependence between a measurable indicator, especially the airway pressure $P_{aw}$ or the esophageal pressure $P_{es}$, as well as the sought pneumatic indicator and other measurable indicators. The term "relationship" is used for the dependence between a sought pneumatic indicator and a respiratory signal as well as for the dependence between a plurality of pneumatic indicators.

A first relationship $\text{Zus}_1$, namely, a relationship between the first pneumatic indicator $P_{mus,1}$ and the first respiratory signal $\text{Sig}_1$ is predefined. This relationship has, for example, the form $$P_{mus,1}(t)=k_1*\text{Sig}_1(t) \tag{2}$$

Here, $k_1$ is a proportionality factor, which preferably has the unit of measurement [mbar/mV] and may also vary with time, but doing so markedly more slowly than the pneumatic indicator $P_{mus,1}$ or the respiratory signal $\text{Sig}_1$. This proportionality factor $k_1$ can be called the neuromuscular efficiency, i.e., it shows how well the muscles of the upper region convert the electrical signals generated in the body of the patient P into muscle movements.

Furthermore, a second relationship $\text{Zus}_2$ is predefined, namely, a relationship between the second pneumatic indicator $P_{mus,2}$ and the second respiratory signal $\text{Sig}_2$. This relationship has, for example, the following form:

$$P_{mus,2}(t)=k_2*\text{Sig}_2(t). \tag{3}$$

In a slight variation, the two relationships have the form $$P_{mus,1}(t)=k_1*\text{Sig}_1(t)+\text{const}, \text{ and } P_{mus,2}(t)=k_2*\text{Sig}_2(t)+\text{const}_2. \tag{4}$$

In addition, a function Fkt is predefined, which describes in one embodiment the airway pressure $P_{aw}$ as a function of the volume (filling level of the lungs) Vol, of the flow rate (change in volume) Vol' and of the overall intrinsic breathing activity $P_{mus}$ of the patient P. This function Fkt has, for example, the form $$P_{aw}(t)=R*\text{Vol}'(t)+E*\text{Vol}(t)+P_{mus}+\text{const}. \tag{5}$$

If Equation (1) holds true, the following function follows from (5):

$$P_{aw}(t)=R*\text{Vol}'(t)+E*\text{Vol}(t)+P_{mus,1}(t)+P_{mus,2}(t)+\text{const.} \qquad (6)$$

The predefined function Fkt or each predefined function Fkt and the predefined relationships $\text{Zus}_1$ and $\text{Zus}_2$ are stored in a computer-accessible form in the memory 9, to which the signal processing unit 5 has reading access.

The lung mechanical factor R describes the breathing resistance, which the airway of the patient P offers to the volume flow Vol'. The lung mechanical factor E describes the elasticity of the lungs. The lung mechanical summand const describes especially the effect of an incomplete exhalation of the patient P.

In one variant, the predefined function (6) is differentiated once in advance according to the time t. As a result, possible time correlations in the residua (deviations of the model from reality) are reduced. Such time residua may lead to worse results when the statistical estimation method is used. In addition, the last summand const disappears due to the differentiation. The function has the following form after the differentiation of (6):

$$P_{aw}'(t)=R*\text{Vol}''(t)+E*\text{Vol}'(t)+P_{mus,1}'(t)+P_{mus,2}'(t). \qquad (7)$$

Figure 5:
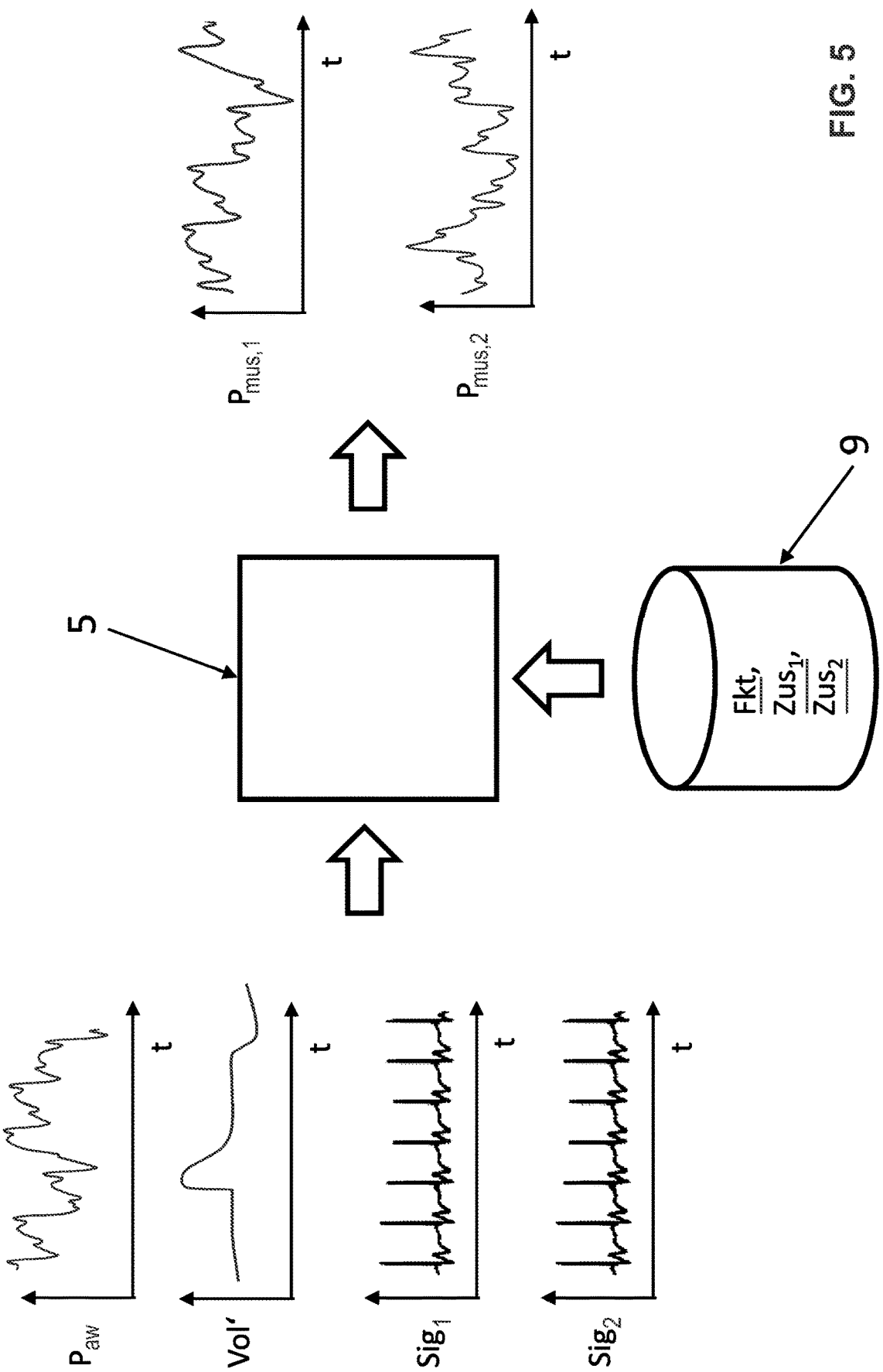
FIG. 5 schematically shows the input signals and the results of the signal processing unit.

FIG. 5 illustrates as an example which measured signals the signal processing unit 5 uses as input signals and which results it yields. The calculations of the signal processing unit 5 are explained in more detail farther below.

Figure 6:
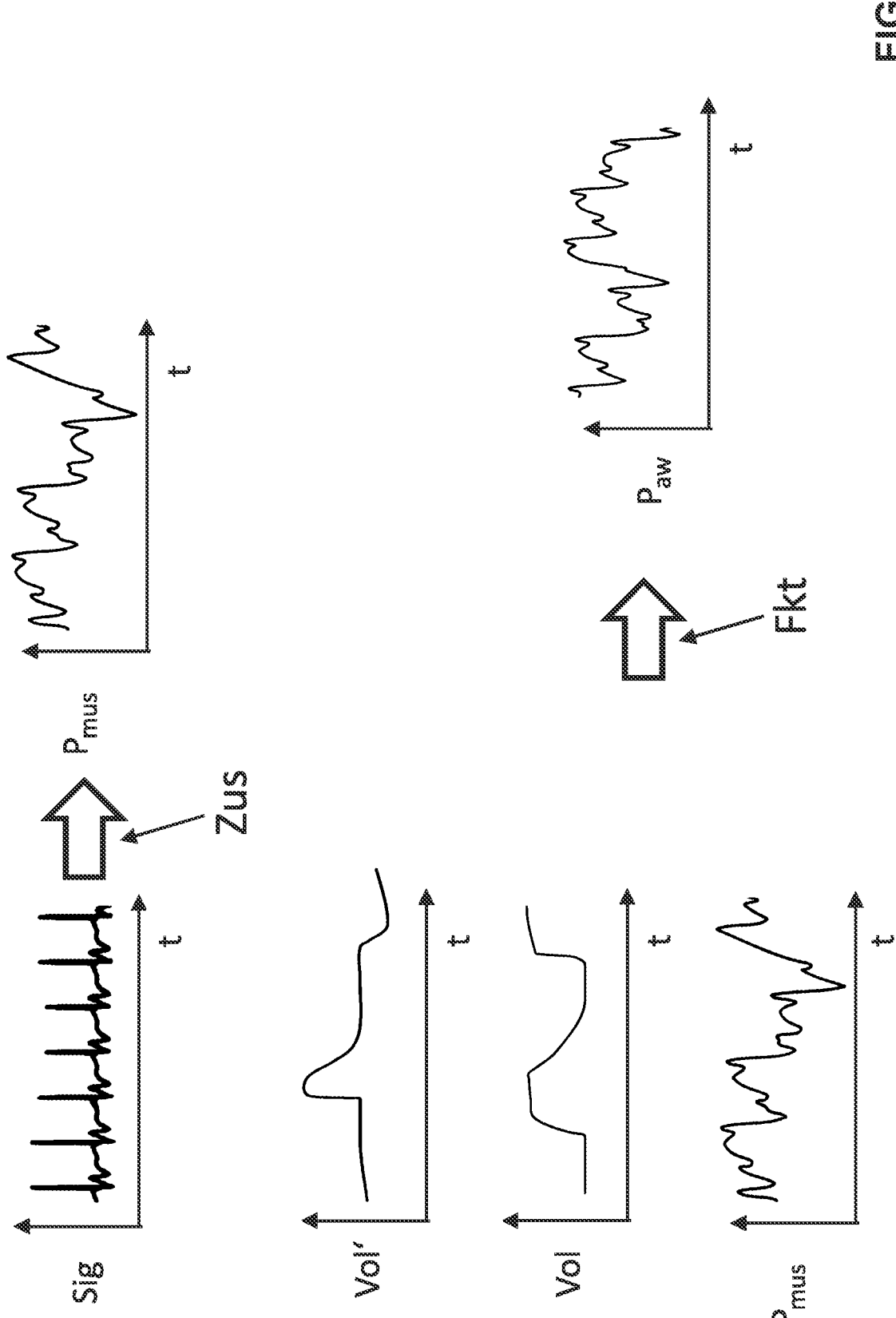
FIG. 6 shows a variant in which an overall relationship and a function are predefined, wherein an overall pneumatic indicator occurs in these two for the breathing activity of the patient.
Figure 7:
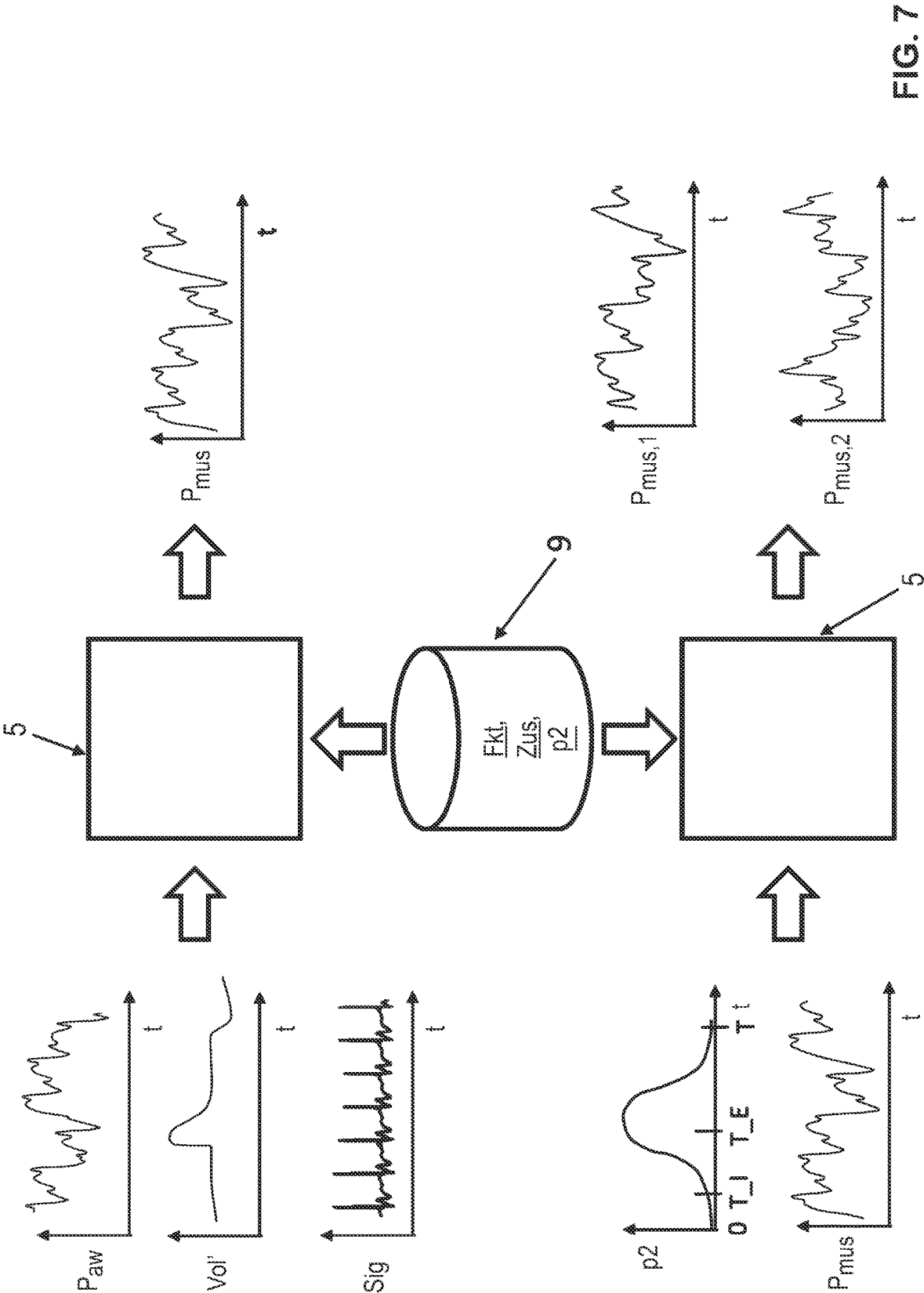
FIG. 7 shows how the overall pneumatic indicator is determined in the variant according to FIG. 6 and how the two pneumatic indicators are determined with the use of a predefined percentage function.

FIG. 6 and FIG. 7 show a variant. A single respiratory overall signal Sig, which is correlated with the overall breathing activity of the patient P and thus with the overall pneumatic indicator $P_{mus}$, is generated from the measured values of the measuring electrodes 2.1.1 through 2.2.2. In addition, as was just described, a respective signal $P_{aw}$ for the airway pressure and a signal Vol' for the volume flow are generated. The overall pneumatic indicator $P_{mus}$ is derived from the overall respiratory signal Sig, and, e.g., the function (5) and the relationship $$P_{mus}(t)=k*\text{Sig}(t) \qquad (8)$$

are used.

In addition, a percentage function p1 or p2 is predefined according to this variant.

A percentage function p2, which approximately describes the percentage which the second region of the breathing muscle contributes to the pneumatic pressure $P_{mus}$ produced by the breathing muscle of the patient P, is predefined in the example shown. This percentage varies over time. Thus, $$P_{mus,2}(t)=p2(t)*P_{mus}(t) \qquad (9)$$

Furthermore, $$P_{mus}(t)=P_{mus,1}(t)+P_{mus,2}(t). \qquad (1)$$

It is also possible, of course, to predefine a percentage function p1, which approximately describes the percentage of the first region. The percentage function describes, e.g., the percentage for the inhalation and the percentage for the exhalation.

The time period from 0 to T covers in the example shown in FIG. 7 a single breath of the patient P. The duration of each breath is standardized for T. The time T_I is the start of the inhalation (inspiration), and the time T_E is the start of the exhalation (expiration). For example, $$P_{aw}(t)=R*\text{Vol}'(t)+E*\text{Vol}(t)+P_{mus}(t)+\text{const} \qquad (5)$$

is predefined as the function Fkt in this case, or, after differentiation of (5), also $$P_{aw}'(t)=R*\text{Vol}''(t)+E*\text{Vol}'(t)+P_{mus}'(t). \qquad (10)$$

In this case, the signal processing unit 5 calculates first values $P_{mus}(t)$ for the pneumatic indicator $P_{mus}$, which describes the overall breathing activity of the patient P, and then, using the percentage function p2(t) and the relationship (9), values $P_{mus,2}(t)$ for the second pneumatic indicator $P_{mus,2}$ as well as values $P_{mus,1}(t)$ for the first pneumatic indicator $P_{mus,1}$ according to $$P_{mus,1}(t)=P_{mus}(t)-P_{mus,2}(t) \qquad (11)$$

from these values.

Figure 8:
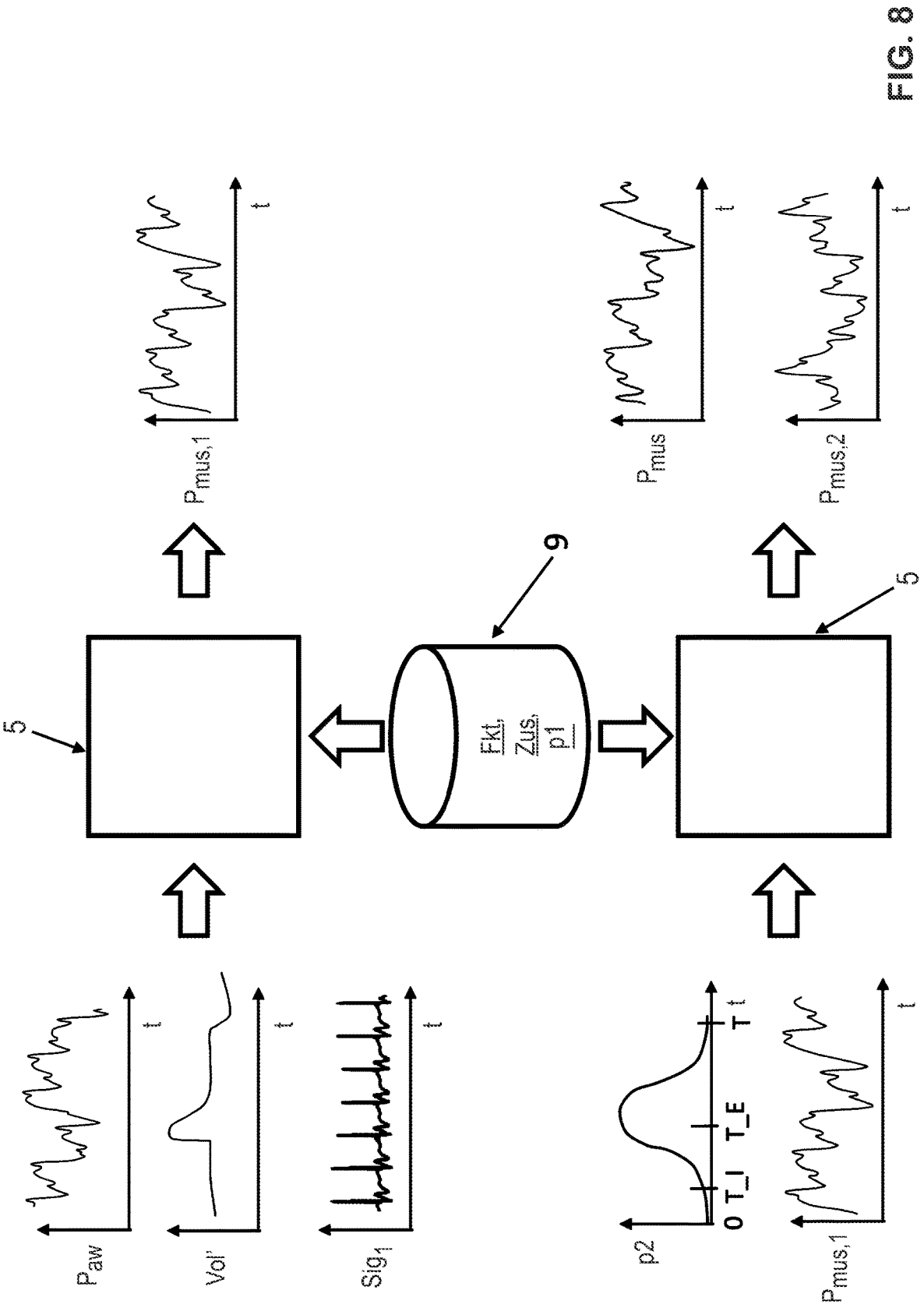
FIG. 8 shows a variant of the variant shown in FIG. 7, in which the first pneumatic indicator is determined and the other pneumatic indicator and the overall pneumatic indicator are then determined with the use of the percentage function.

FIG. 8 illustrates a variant of the procedure illustrated by FIG. 7. A first respiratory signal $\text{Sig}_1$, which is correlated with the first pneumatic indicator $P_{mus,1}$, is generated in the variant according to FIG. 8. For example, measuring electrodes, which are positioned on the skin of the patient P close to the first region, are used to generate the first respiratory signal $\text{Sig}_1$. Furthermore, a percentage function p1(t), which describes the percentage for the first pneumatic indicator $P_{mus,1}$ in the overall pneumatic indicator $P_{mus}$, is predefined as was described above.

$$p1(t)+p2(t)=1 \qquad (12)$$

and $$P_{mus}(t)=P_{mus,1}(t)+P_{mus,2}(t) \qquad (1)$$

and hence $$P_{mus}(t)=P_{mus,1}(t)/[1-p1(t)] \qquad (13)$$

preferably holds true for each time t.

To generate the first respiratory signal $\text{Sig}_1$ according to the variant shown in FIG. 8, the relationship (11) is introduced into the function (5) in one embodiment, which leads to the function $$P_{aw}(t)=R*\text{Vol}'(t)+E*\text{Vol}(t)+P_{mus,1}(t)/[1-p1(t)]-\text{const.} \qquad (14)$$

It is possible, in turn, to use the relationship based on the derivation. In addition, the relationship (2) is used. After the first pneumatic indicator $P_{mus,1}$ has been determined, the second pneumatic indicator $P_{mus,2}$ is determined with the use of (1).

It is also possible to determine the second pneumatic indicator $P_{mus,2}$ from a second respiratory signal $\text{Sig}_2$ and then the overall pneumatic indicator and/or the first pneumatic indicator $P_{mus,1}$. The two variants, in which two respiratory signals $\text{Sig}_1$ and $\text{Sig}_2$ are generated from measured values, and in which a percentage function p1 or p2 is used, may be combined with one another, for example, in order to carry out a plausibility check or to obtain two results, between which an averaging will then be performed in a suitable manner. Consequently, as is described in the relationship (7) and as is illustrated by FIG. 5, values $P_{mus,1}(t)$ and $P_{mus,2}(t)$ are calculated in this combination for the two pneumatic indicators $P_{mus,1}$ and $P_{mus,2}$, for which measured values of two sets 2.1.1 and 2.1.2 of measuring electrodes as well as two additional sets 2.2.1 and 2.2.2 of measuring electrodes are used. On the other hand, the relationship $$P_{mus,2}(t)=p2(t)*P_{mus,1}(t)=p2(t)*[P_{mus,1}(t)+P_{mus,2}(t)] \qquad (9)$$

is used with predefined percentage function.

In another variant, two functions $\text{Fkt}_{in}$ and $\text{Fkt}_{ex}$ of the same kind are used, which describe the airway pressure as a function of other indicators, wherein the one function $Fkt_{in}$ applies to the inhalation (inspiration, subscript in) and the other function $Fkt_{ex}$ to the exhalation (expiration, subscript ex). These two functions have, for example, the following form:

$$P_{aw,in}(t)=R_{in}*\text{Vol}'(t)+E_{in}*\text{Vol}(t)P_{mus,1,in}(t)+P_{mus,2,in}(t) \\ \text{const}_{in}, \tag{15}$$

and $$P_{aw,ex}(t)=R_{ex}*\text{Vol}_{ex}(t)+E_{ex}*\text{Vol}(t)+P_{mus,1,ex}(t)+ \\ P_{mus,2,ex}(t)+\text{const}_{ex}, \tag{16}$$

i.e., they are very similar to the relationship (6) with model parameters, which may assume different values for inhalation and for exhalation. Two respective relationships are correspondingly used for inhalation and for exhalation:

$$P_{mus,1,in}(t)=k_{1,in}*\text{Sig}_{1,in}(t) \tag{17}$$

and $$P_{mus,2,in}(t)=k_{2,in}*\text{Sig}_{2,in}(t) \tag{18}$$

and $$P_{mus,1,ex}(t)=k_{1,ex}*\text{Sig}_{1,ex}(t) \tag{19}$$

and $$P_{mus,2,ex}(t)=k_{2,ex}*\text{Sig}_{2,ex}(t). \tag{20}$$

The hypothesis that at any time, the patient P
is either inhaling or exhaling and the function (15) and the relationships (17) and (18) apply to the inhalation or the function (16) and the relationships (19) and (20) apply to the exhalation
or the patient P is not currently either inhaling or exhaling
is used in one variant.

The inhalation and the exhalation can be elicited by the breathing muscles of the patient P and/or by the mechanical ventilation.

It is taken into consideration in another variant that signals based on inhalation and signals based on exhalation may be superimposed at one time, for example, because the mechanical ventilation is not synchronized perfectly with the spontaneous breathing of the patient P. The following relationship is used in that case:

$$P_{aw}(t)=R_{in}*\text{Vol}_{in}'(t)+R_{ex}*\text{Vol}_{ex}'(t)+E_{in}*\text{Vol}_{in}(t)+ \\ E_{ex}*\text{Vol}_{ex}(t)+P_{mus,1}(t)+P_{mus,2}(t)+\text{const}_{in}. \tag{21}$$

The inspiratory and expiratory contributions cannot be measured directly, but the volume flow Vol'(t) and/or the volume Vol(t) can. The further relationships $$\text{Vol}'(t)=\text{Vol}_{in}'(t)+\text{Vol}_{ex}'(t) \tag{22}$$

and $$\text{Vol}(t)=\text{Vol}_{in}(t)+\text{Vol}_{ex}(t) \tag{23}$$

are used.

A function with additional summands, for example, the following function:

$$P_{aw}(t)=R*\text{Vol}'(t)+E*\text{Vol}(t)+I*\text{Vol}''(t)+Q*\text{Abs} \\ [\text{Vol}'(t)]*\text{Vol}'(t)+S*\text{Vol}^2(t)+P_{mus,1}(t)+P_{mus,2}(t)+ \\ \text{const} \tag{24}$$

is predefined and used in another embodiment instead of the function (5).

Here, Q describes the resistance to the air flow, which is generated by the turbulent flow in a hose from the ventilator 1 to the patient P and/or in the esophagus of the patient P, S is the change in the compliance of the lungs and/or in the expansion of the thorax as a function of the volume Vol, and I is the resistance to the acceleration, wherein this resistance is negligibly low in case of a sufficiently low acceleration.

Figure 9:
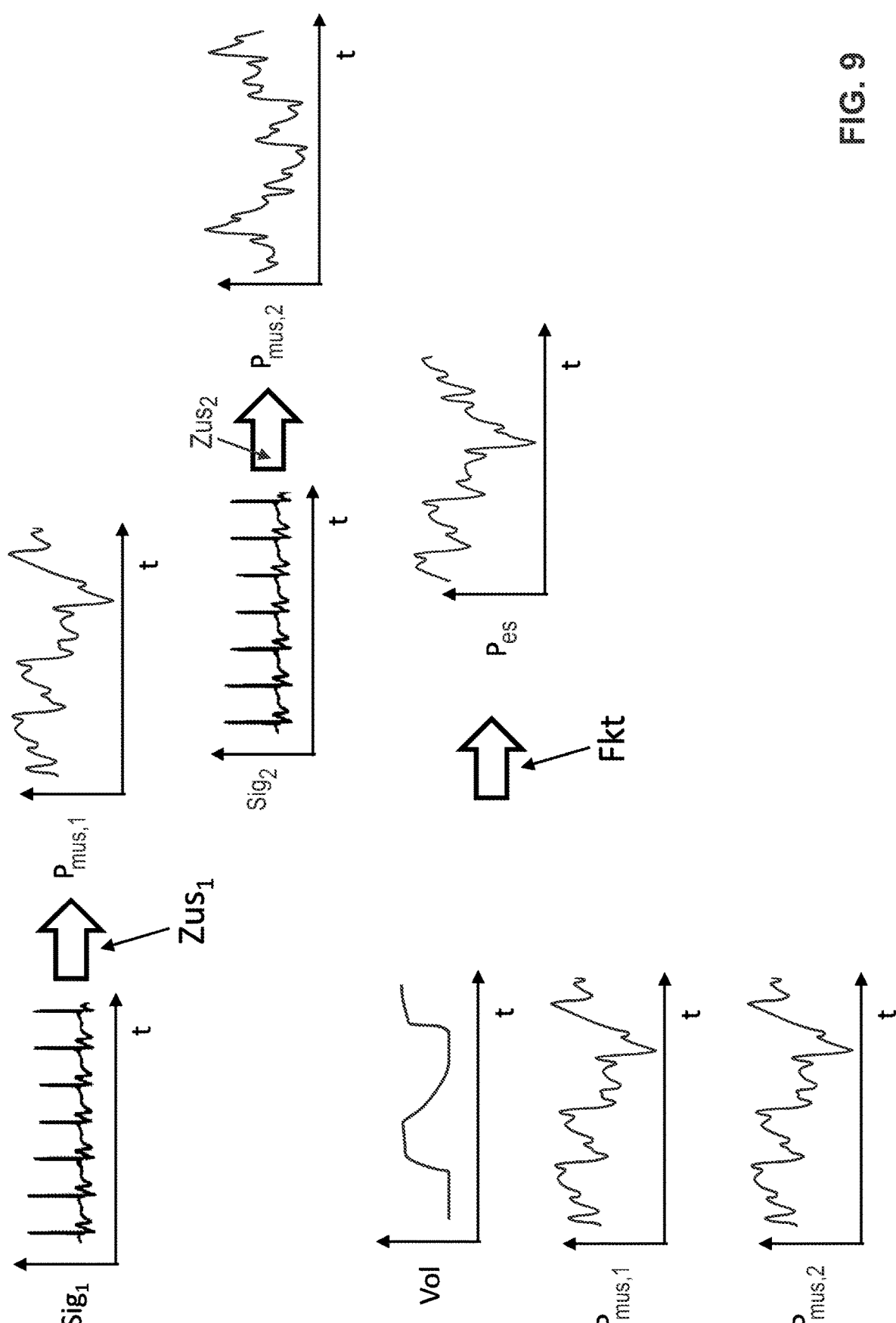
FIG. 9 shows a variant in which the pressure in the esophagus is measured instead of the airway pressure.

FIG. 9 schematically shows a variant in which the pressure $P_{es}$ in the esophagus of the patient P is measured, instead of the airway pressure $P_{aw}$, specifically by means of the probe 6. For example, the following function is predefined as the function Fkt:

$$P_{es}(t)=E_{cw}*\text{Vol}(t)-P_{mus,1}(t)-P_{mus,2}(t)+\text{const} \tag{25}$$

or also $$P_{es}'(t)=E_{cw}*\text{Vol}'(t)-P_{mus,1}'(t)-P_{mus,2}'(t) \tag{26}$$

after the function (25) was differentiated according to time. The factor $E_{cw}$ describes the elasticity based on the chest wall (chestwall) of the patient P.

Both the function or each predefined function Fkt and the two predefined relationships $Zus_1$ and $Zus_2$ apply, as a rule, only approximately. Therefore, and because parameters with unknown values, which are variable over time, occur, the pneumatic indicators are not determined exclusively with the use of respiratory signals and relationships. The function or at least one function as well as additional signals are rather used additionally.

In one embodiment, three deviations (residua) $\text{Res}_{Fkt}(t)$, $\text{Res}_1(t)$ and $\text{Res}_2(t)$ are taken into consideration, wherein $$\text{Res}_{Fkt}(t)=P_{aw}(t)-R*\text{Vol}'(t)-E*\text{Vol}(t)-P_{mus,1}(t)- \\ P_{mus,2}(t)-\text{const}, \tag{27}$$

$$\text{Res}_1(t)=P_{mus,1}(t)-k_1*\text{Sig}_1(t) \tag{28}$$

and $$\text{Res}_2(t)=P_{mus,2}(t)-k_1*\text{Sig}_2(t). \tag{29}$$

After introduction of the two relationships (2) and (3) into (27), this leads to an overall deviation $$\text{Res}_{ges}(t)=P_{aw}(t)-R*\text{Vol}'(t)-E*\text{Vol}(t)-k_1*\text{Sig}_1(t)- \\ k_2*\text{Sig}_2(t)-\text{const} \tag{30}$$

or also $$\text{Res}_{ges}(t)=P_{aw}'(t)-R*\text{Vol}''(t)-E*\text{Vol}'(t)-P_{mus,1}'(t)- \\ P_{mus,2}'(t) \tag{31}$$

The two relationships $Zus_1$ and $Zus_2$, i.e., (2) and (3) or (17) through (20), as well as the function Fkt, i.e., (6) or (7) or (15) and (16) or (21) or (25), form together a model for the breathing activity of the patient P. In one embodiment, this model has a plurality of model parameters. In the relationships and functions just introduced, these are the factors R, E, $E_{cw}$, $k_1$ and $k_2$ as well as the summand constant, which depends, among other things, on the volume remaining in the lungs after exhalation. The values of these model parameters vary, as a rule, over time. Estimated values, namely, a respective set of values each at each scanning time $t_i$, are derived for these model parameters.

A scanning time window is predefined in one embodiment, and the values, which the model parameters assume in this scanning time window, are calculated. This scanning time window migrates over time and comprises in one embodiment N+1 consecutive scanning times $t_{i-N}$ through $t_i$, wherein t is the current scanning time. The measurements and the subsequent signal processing yield N+1 sets of signal values for the measurable indicators, and each set of signal values pertains to a scanning time $t_i$ each.

For example, each signal value set has the form $$[P_{aw}(t_i),\text{Vol}(t_i),\text{Sig}_i(t_i),\text{Sig}_2(t_i)]$$

or also $$[P_{aw}'(t_i),\text{Vol}''(t_i),\text{Sig}_1'(t_i),\text{Sig}_2'(t)],$$

wherein $t_i$ is a scanning time (i=1, 2, 3, . . . ).

A regression analysis is carried out to minimize the overall deviation $\text{Res}_{ges}(t)$ in the scanning time window. The N+1 signal value sets from the scanning time window are used for this. In one embodiment, each signal value set is provided with a weighting factor, and the older the signal value set, the lower is the weighting factor. In another embodiment, all signal value sets have the same weighting factor 1/(N+1).

The regression analysis yields for each model parameter a respective estimated value (subscript est), i.e., for example, the values $R_{est}$, $E_{est}$, $E_{CW,est}$, $k_{1,est}$, $k_{2,est}$ and optionally $\text{const}_{est}$. Each model parameter value is valid for the scanning time window. A model parameter in a subsequent scanning time window may assume a different value.

Now, $$P_{mus,1}(t)=k_{1,est}{*}\text{Sig}_1(t), \tag{32}$$

$$P_{mus,2}(t)=k_{2,est}{*}\text{Sig}_2(t) \tag{33}$$

and $$P_{aw}(t)=R_{est}{*}\text{Vol}'(t)+E_{est}{*}\text{Vol}(t)+P_{mus,1}(t)+P_{mus,2}(t)+\text{const}_{est} \tag{34}$$

will approximately hold true, with the unknowns $P_{mus,1}(t)$ and $P_{mus,2}(t)$.

The signal processing unit 5 repeats these calculations continually, preferably for the respective, chronologically last N+1 number of scanning times. It is possible that the number of N+1 varies from one scanning time window to the next.

Figure 10:
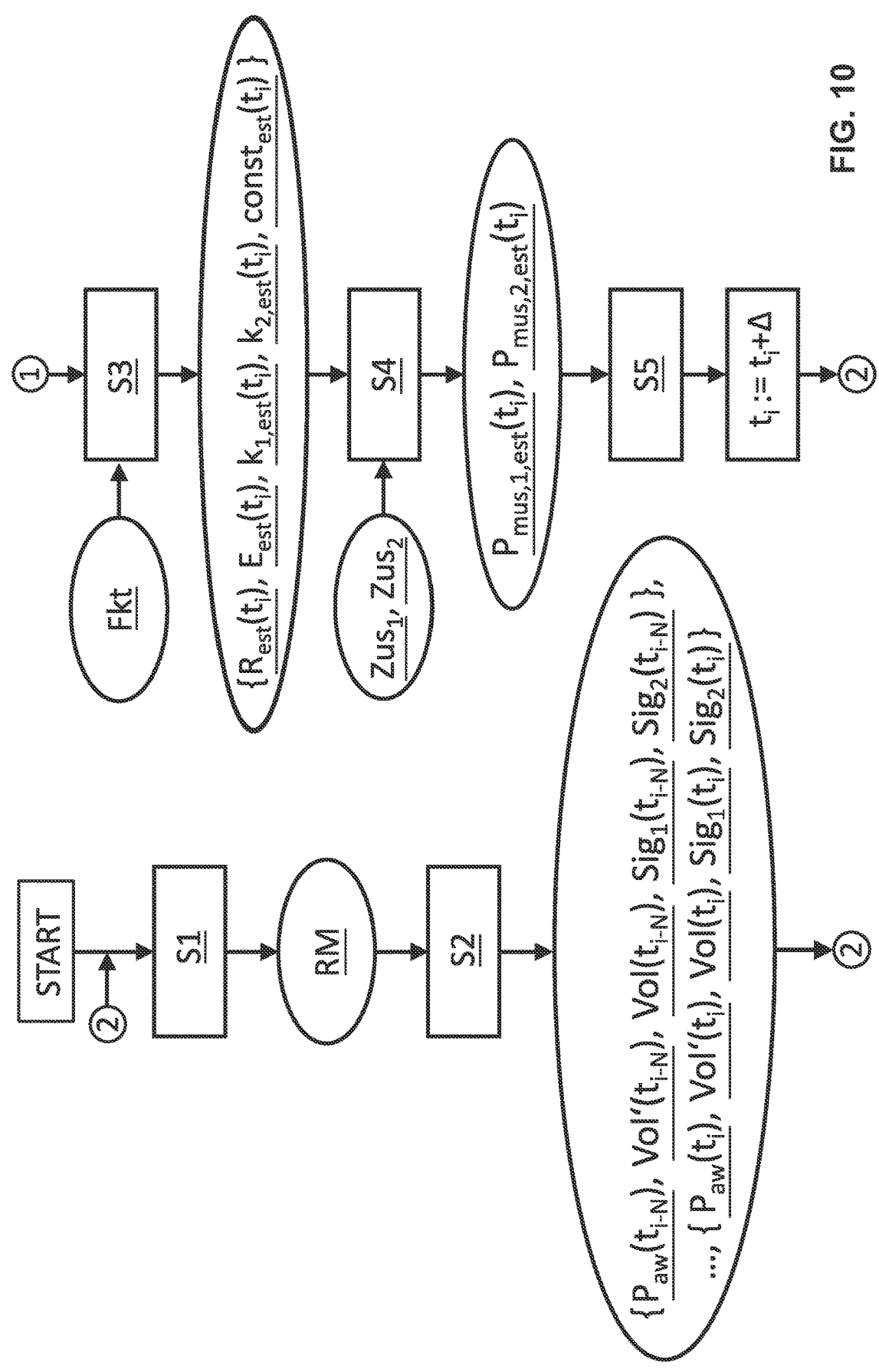
FIG. 10 shows on the basis of a flow chart how values are continually calculated for the two pneumatic indicators.

FIG. 10 illustrates on the basis of a flow chart, for example, steps that are carried out to calculate two values at the current scanning time t for the two pneumatic indicators $P_{mus,1}$ and $P_{mus,2}$. It is shown clearly that the values of the model parameters are also variable over time and are considered to be constant only within a scanning time window up to the current scanning time $t_i$.

FIG. 10 shows the following steps and results:
In step S1, the signal processing unit 5 receives at the current scanning time $t_i$ a plurality of raw measured values from the sensors 2.1.1 through 2.2.2 and 3 and optionally from the sensor 4.

In step S2, the signal processing unit 5 processes the measured values, e.g., as shown in FIG. 3. The signal processing unit 5 generates in step S2 a set of signal values, which pertains to the current scanning time $t_i$.

The signal processing unit 5 derives in step S3 a set of model parameter values. It uses for this the current signal value set $\{P_{aw}(t_i), \text{Vol}'(t_1), \text{Vol}(t), \text{Sig}_1(t), \text{Sig}_2(t)\}$ from step S2 as well as N preceding signal value sets $$\{P_{aw}(t_{i-N}),\text{Vol}(t_{i-N}),\text{Sig}_1(t_{i-N}),\text{Sig}_2(t_{i-N})\}, \quad . \quad . \quad . \quad ,$$
$$\{P_{aw}(t_{i-1}),\text{Vol}'(t_{i-i}),\text{Vol}(t_{i-1}),\text{Sig}_1(t_{i-1}),\text{Sig}_2(t_{i-1})\}$$

of N preceding scanning times $t_{i-N}$, . . . , $t_{i-1}$. The scanning time window consequently comprises N+1 scanning times.

In addition, the signal processing unit 5 uses a predefined function Fkt, for example, one of the functions introduced farther above.

Step S3 yields the set $\{R_{est}(t_i),\ E_{est}(t_i),\ k_{1,est}(t_i),\ k_{2,est}(t_i),\ \text{const}_{est}(t_i)\}$ of model parameter values.

The signal processing unit 5 calculates in step S4 the two values $P_{mus,1,est}(t_i)$, $P_{mus,2,est}(t_i)$ for the two pneumatic indicators $P_{mus,1}$ and $P_{mus,2}$. The signal processing unit 5 uses for this the set of model parameter values derived in step S3 as well as the two predefined relationships $\text{Zus}_1$ and $\text{Zus}_2$.

The signal processing unit 5 uses in step S5 the two values $P_{mus,1,est}(t_i)$ and $P_{mus,2,est}(t_i)$, for example, in order to actuate the ventilator 1 and/or in order to actuate the output unit, on which the two indicators $P_{mus,1,est}(t_i)$ and $P_{mus,2,est}(t_i)$ as well as previous values of the two pneumatic indicators are displayed in a form perceptible by a person.

These steps S1 through S5 are carried out again for the next scanning time $t_i+1=t_i+\Delta$.

In one variant, the inhalation and the exhalation are detected and distinguished from one another by calculation. The signal processing unit 5 uses N1 inspiratory signal value sets, which have been measured during the inhalation by the patient P, on the one hand, and, on the other hand, N2 expiratory signal value sets, which have been measured during the exhalation by the patient P. The two numbers N1 and N2 may be equal or different from one another. The signal processing unit 5 applies at each scanning time, or other calculation time, a regression analysis, on the one hand, to the N1 inspiratory signal value sets, in order to derive an estimated model parameter value valid during the inhalation for each model parameter, for example, values for $R_{in,est}$, $E_{in,est}$, $k_{1,in,est}$ and $k_{2,in,est}$, and optionally $\text{const}_{in,est}$. The signal processing unit 5 calculates by means of these model parameter values and the function (10) as well as the relationship (12) a respective value $P_{mus,1,in}(t)$ for the first pneumatic indicator $P_{mus,1,in}$ and a value $P_{mus,2in}(t)$ for the second pneumatic indicator $P_{mus,2,in}$, which hold true for the inhalation. The signal processing unit 5 also performs the corresponding procedure, on the other hand, for the exhalation in order to calculate values for the two pneumatic indicators $P_{mus,1,ex}$ and $P_{mus,2,ex}$, and it uses for this the function (11) as well as the relationship (13).

The first two pneumatic indicators $P_{mus,1,in}$ and $P_{mus,1,ex}$, which are valid for the inhalation and for the exhalation, respectively, are used separately from one another in one application. In another application, a first overall pneumatic indicator is derived from the first two pneumatic indicators $P_{mus,1,in}$ and $P_{mus,1,ex}$ for the inhalation and for the exhalation. This also applies analogously to the two second pneumatic indicators $P_{mus,2,in}$ and $P_{mus,2,ex}$.

While specific embodiments of the invention have been shown and described in detail to illustrate the application of the principles of the invention, it will be understood that the invention may be embodied otherwise without departing from such principles.

LIST OF REFERENCE NUMBERS

1 Ventilator, mechanically ventilating the patient P; it comprises the signal processing unit 5
2.1.1, 2.1.2 First set of measuring electrodes on the skin of the patient P; it yields the measured values for the signal $\text{Sig}_2$, which is correlated with the second pneumatic indicator $P_{mus,2}$
2.2.1, 2.2.2 Second set of measuring electrodes on the skin of the patient P; it yields the measured values for the signal $\text{Sig}_1$, which is correlated with the first pneumatic indicator $P_{mus,1}$
3 Pneumatic sensor in front of the mouth of the patient P; it measures the airway pressure $P_{aw}$

4 Optical sensor with an image recording device and with an image analysis unit; it measures the geometry of the body of the patient P, from which the current filling level of the lungs Vol is derived by calculation

5 Signal processing unit; it carries out the steps of the process according to the present invention

6 Probe in the esophagus Sp; it measures the pneumatic pressure $P_{es}$ in the esophagus Sp

9 Memory, in which the function Fkt and the relationships $Zus_1$ and $Zus_2$ are stored and to which the signal processing unit 5 has read access const Model parameter in the form of a lung mechanical summand: Residual pressure after an incomplete exhalation by the patient P $const_{est}(t_i)$ Estimated value of the model parameter const at the scanning time $t_i$ $\Delta$ Distance between two consecutive scanning times $t_i$ and $t_i+1$ E Model parameter in the form of a lung mechanical factor: Elasticity of the lungs of the patient P $E_{cw}$ Elasticity based on the chest wall (chestwall) of the patient P $E_{est}(t_i)$ Estimated value of the model parameter E at the scanning time $t_i$ Fkt Predefined function, measurable pneumatic indicator $P_{aw}$ or $P_{es}$ for the airway pressure as a function of Vol, Vol', $P_{mus,1}$, $P_{mus,2}$ $k_1$ Neuromuscular efficiency of the first region of the breathing muscles; it is a model parameter $k_{1,est}(t_i)$ Estimated value of the model parameter $k_1$ at the scanning time $t_i$ $k_2$ Neuromuscular efficiency of the second region of the breathing muscles; it is a model parameter $k_{2,est}(t_i)$ Estimated value of the model parameter $k_2$ at the scanning time $t_i$ N+1 Number of scanning times of a scanning time window P Patient with the esophagus Sp and with the diaphragm Zw; P is ventilated mechanically by the ventilator 1

$P_{aw}$ Airway pressure, generated by the intrinsic breathing activity of the patient P and by the mechanical ventilation by the ventilator 1; measured by sensor 3

$P_{es}$ Pressure in the esophagus Sp of the patient P; it is measured with a probe 6 in the esophagus Sp $P_{mus}$ Overall pneumatic indicator for the overall breathing activity of the patient P $P_{mus}(t_i)$ Value of the overall pneumatic indicator $P_{mus}$ at the scanning time $t_i$ $P_{mus,1}$ First pneumatic indicator; it describes the breathing activity of the first region, e.g., of the diaphragm Zw or of the left half of the body, or during a first process $P_{mus,1,in}$ First pneumatic indicator applicable to the inhalation (inspiration)

$P_{mus,1,ex}$ First pneumatic indicator applicable to the exhalation (expiration)

$P_{mus,1}(t_i)$ Value of the first pneumatic indicator $P_{mus,1}$ at the scanning time $t_i$ $P_{mus,2}$ Second pneumatic indicator; it describes the breathing activity of the second region, e.g., of the breathing muscles or of the right half of the body, or during a second process $P_{mus,2,in}$ Second pneumatic indicator applicable to the inhalation (inspiration)

$P_{mus,2,ex}$ Second pneumatic indicator applicable to the exhalation (expiration)

$P_{mus,2}(t_i)$ Value of the second pneumatic indicator $P_{mus,2}$ at the scanning time $t_i$ R Model parameter in the form of a lung mechanical factor: Breathing resistance, which the airway of the patient P offers against the volume flow Vol'

$R_{est}(t_i)$ Estimated value of the model parameter R at the scanning time $t_i$ RM Time curve of the raw measured values, from which a signal is calculated S1 Step: Raw measured values RM received S2 Step: Generate the signal value set $\{P_{aw}(ti), Vol'(ti), Vol(ti), Sig_1(ti), Sig_2(ti)\}$ from the raw measured values RM S3 Step: Derive the set $\{R_{est}(t), E_{est}(t_i), k_{1,est}(t_i), k_{2,est}(t_i), const_{es}(t_i)\}$ of model parameter values with the use of the N+1 signal value sets of the scanning time window and of the predefined function Fkt S4 Step: Calculate the two values $P_{mus,1,est}(t_i)$ and $P_{mus,2,es}(t_i)$ for the two pneumatic indicators with the use of the set of model parameter values and of the predefined relationships $Zus_1$ and $Zus_2$ S5 Step: Use the calculated values $P_{mus,1,est}(t_i)$ and $P_{mus,2,est}(t_i)$ Sig Overall electrical respiratory signal for the overall intrinsic breathing activity of the patient P; it is correlated with the overall pneumatic indicator $P_{mus}$ $Sig_1$ Electrical respiratory signal for the first region of the respiratory system of the patient P; it is correlated with the first pneumatic indicator $P_{mus,1}$ $Sig_2$ Electrical respiratory signal for the second region of the respiratory system of the patient; it is correlated with the second pneumatic indicator $P_{mus,2}$ Sp Esophagus of the patient P T_E Time at which the patient P begins to exhale (expiration)

T_I Time at which the patient P begins to inhale (inspiration)

$t_i$ Scanning time

Vol Volume (current filling level) of the lungs of the patient; it is the integral of the volume flow Vol' over time; measured in one embodiment by the optical sensor 4

Vol' Flow of air into and out of the lungs of the patient P per unit of time; it is the derivation of the volume Vol according to the time; measured, e.g., from the sensor 3

$Zus_1$ Predefined relationship between the first respiratory signal $Sig_1$ and the first pneumatic indicator $P_{mus,1}$ $Zus_2$ Predefined relationship between the second respiratory signal $Sig_2$ and the second pneumatic indicator $P_{mus,2}$ Zw Diaphragm of the patient P

The invention claimed is:

1. A process for determining a first pneumatic indicator and a second pneumatic indicator for the breathing activity of a patient, wherein the first pneumatic indicator describes activity of a first region of a respiratory system of the patient and/or of a first process during breathing by the patient and the second pneumatic indicator describes activity of a second region of the respiratory system of the patient and/or of a second process during the breathing by the patient, the second region being different from the first region and/or the second process being different from the first process, wherein a predefined airway pressure function, which describes a measurable indicator for an airway pressure, wherein the airway pressure is achieved by an overall intrinsic breathing activity of the patient and/or by mechanical ventilation of the patient, is predefined in a computer-accessible form as a function of at least:

a volume flow indicator for a volume flow of breathing air relative to the patient and/or a filling level indicator for a filling level of the lungs of the patient as well as a function of the first pneumatic indicator and the second pneumatic indicator to be determined and/or of an overall pneumatic indicator for the overall breathing activity of the patient, wherein a first relationship between the first pneumatic indicator and a first measurable respiratory signal and/or a second relationship between the second pneumatic indicator and a second measurable respiratory signal and/or an overall relationship between the overall pneumatic indicator for the overall breathing activity of the patient and an overall measurable respiratory signal are pre-defined in a computer-accessible form, wherein at least one of the first and second relationships and/or the overall relationship has a model parameter and wherein the process comprises steps that the patient is at least temporarily connected to an airway pressure sensor, which measures the measurable indicator for the airway pressure, a signal processing unit receives measured values of the airway pressure sensor while the patient is connected to the airway pressure sensor and generates an airway pressure signal with the use of at least some of the values measured by the airway pressure sensor and uses a predefined value for the airway pressure as an airway pressure signal while the patient is not connected to the airway pressure sensor, the signal processing unit receives values measured by a volume flow sensor during the overall intrinsic breathing activity of the patient and/or the mechanical ventilation of the patient, the volume flow sensor measures the volume flow indicator for the volume flow of breathing air and generates a volume flow signal from at least some of the values measured by the volume flow sensor, and/or receives values measured by a filling level sensor during the overall intrinsic breathing activity of the patient and/or the mechanical ventilation of the patient, the filling level sensor measures the filling level indicator for the filling level of the lungs of the patient, and generates a volume signal from at least some of the values measured by the filling level sensor, a first and/or a second and/or a third sequence are carried out during the overall intrinsic breathing activity of the patient and/or the mechanical ventilation of the patient:

in the first sequence, the signal processing unit receives values measured by a first breathing sensor, wherein the measured values pertain to an indicator that is correlated with the first pneumatic indicator, generates the first measurable respiratory signal from at least some of the values measured by the first breathing sensor, derives a value for the model parameter, which occurs in the first relationship, with the use of the airway pressure function and of generated signals, which signals occur in the airway pressure function, and determines the first pneumatic indicator with the use of the first relationship and of the value of the model parameter occurring in the first relationship, in the second sequence the signal processing unit receives values measured by a second breathing sensor, wherein the measured values pertain to an indicator that is correlated with the second pneumatic indicator, generates the second measurable respiratory signal from at least some of the values measured by the second breathing sensor, derives a value for the model parameter that occurs in the second relationship with the use of the airway pressure function and of generated signals, which signals occur in the airway pressure function, and determines the second pneumatic indicator with the use of the second relationship and of the respective value of the model parameter occurring in the second relationship, in the third sequence the signal processing unit receives measured values from an overall breathing sensor, wherein the measured values pertain to an indicator that is correlated with the overall pneumatic indicator, generates the overall measurable respiratory signal from values measured by the overall breathing sensor, derives a value for the model parameter that occurs in the overall relationship with the use of the airway pressure function and of generated signals, which signals occur in the airway pressure function, and determines the overall pneumatic indicator with the use of the overall relationship and of the derived value of the model parameter occurring in the overall relationship, wherein the signal processing unit is configured such that in the case that one of the first pneumatic indicator or the second pneumatic indicator as well as the overall pneumatic indicator have been determined, but the other one of the first pneumatic indicator or the second pneumatic indicator has not been determined, the signal processing unit determines the other one of the first pneumatic indicator or the second pneumatic indicator with the use of the one of the first pneumatic indicator or the second pneumatic indicator already determined and of the overall pneumatic indicator already determined, wherein the signal processing unit is configured such that in the case that the one of the first pneumatic indicator or the second pneumatic indicator has been determined but neither the overall pneumatic indicator nor the other one of the first pneumatic indicator or the second pneumatic indicator have been determined, the signal processing unit determines the overall pneumatic indicator with the use of the one of the first pneumatic indicator or the second pneumatic indicator that has been determined as well as the volume flow signal; and/or the volume signal and/or a predefined percentage function, and determines the other one of the first pneumatic indicator or the second pneumatic indicator with the use of the one of the first pneumatic indicator or the second pneumatic indicator that has been determined and the overall pneumatic indicator, and wherein the signal processing unit is configured such that in the case that the overall pneumatic indicator has been determined, but neither the first pneumatic indicator nor the second pneumatic indicator has been determined, the signal processing unit determines the first pneumatic indicator and the second pneumatic indicator with the use of the overall pneumatic indicator as well as of the volume flow signal and/or of the volume signal and/or of the predefined percentage function.

2. A process in accordance with claim 1, wherein in the step of deriving the respective value for the model parameter, the signal processing unit applies a statistical method to the airway pressure function, to the first and/or the second and/or the overall relationship and/or to the signals.

3. A process in accordance with claim 1, wherein the first relationship and/or the second relationship and/or the overall relationship is a transfer function, which depends linearly on the model parameter of this relationship.

4. A process in accordance with claim 1, wherein the airway pressure function has the model parameter, and the signal processing unit additionally calculates a value for the model parameter of the airway pressure function depending on at least one signal.

5. A process in accordance with claim 4, wherein the airway pressure function describes the measurable indicator for the airway pressure as a function of
the volume flow,
the filling level of the lungs as well as
the first pneumatic indicator and the second pneumatic indicator or the overall pneumatic indicator
and further as a function of at least
a weighting factor for the volume flow and
a weighting factor for the filling level of the lungs,
wherein the weighting factor for the volume flow is a first model parameter and the weighting factor for the filling level of the lungs is a second model parameter of the airway pressure function.

6. A process in accordance with claim 1, wherein the signal processing unit
receives the values measured by the first breathing sensor, wherein the first breathing sensor measures an indicator correlating with the first pneumatic indicator, and generates the first measurable respiratory signal from the values measured by the first breathing sensor and
receives the measured values from the second breathing sensor, wherein the second breathing sensor measures an indicator correlating with the second pneumatic indicator, and generates the second measurable respiratory signal from values measured by the second breathing sensor.

7. A process in accordance with claim 6, wherein the signal processing unit receives
the measured values from a first measuring electrode, and
the measured values from a second measuring electrode, wherein the first measuring electrode
is used as part of the first breathing sensor, which provides the measured values for the first measurable respiratory signal, and
is positioned in a first region on the skin of the patient and wherein the second measuring electrode
is used as part of the second breathing sensor, which provides the measured values for the second measurable respiratory signal, and
is positioned in a second region on the skin of the patient, wherein the second region is located at a spatial distance from the first region.

8. A process in accordance with claim 6, wherein an additional function, which describes the overall pneumatic indicator for an overall activity of the respiratory system of the patient as a function of the first pneumatic indicator and of the second pneumatic indicator, is predefined in a computer-accessible form,
wherein the process comprises additional steps that the signal processing unit
generates an overall respiratory signal, which is correlated with the overall pneumatic indicator,

uses at least temporarily measured values of the airway pressure sensor, the measured values of the volume flow sensor and/or measured values of the volume sensor for generating the overall measurable respiratory signal
and additionally uses the additional function and the overall measurable respiratory signal for determining the first pneumatic indicator and the second pneumatic indicator.

9. A process in accordance with claim 1, wherein the signal processing unit
determines the overall pneumatic indicator and
determines the first pneumatic indicator and the second pneumatic indicator from the overall pneumatic indicator and additionally from the volume flow signal and/or from the volume signal,
and determines a percentage of the overall pneumatic indicator that is taken by the first pneumatic indicator and/or by the second pneumatic indicator.

10. A process in accordance with claim 1, wherein the signal processing unit
generates both the volume signal from the measured values of the filling level sensor and the volume flow signal from measured values of the volume flow sensor and
uses both the volume flow signal and the volume signal in the steps of deriving the respective value for at least one of the model parameters.

11. A process in accordance with claim 1, wherein a computer-accessible geometric relationship between the filling level of the lungs of the patient and a measurable indicator for a geometry of the body of the patient is predetermined, wherein the filling level sensor comprises a geometry sensor, wherein the geometry sensor measures the measurable indicator for the body geometry, and
wherein the signal processing unit
receives measured values from the geometry sensor,
determines a current filling level indicator for the current filling level of the lungs of the patient by applying the computer-accessible geometric relationship to the measured values of the geometry sensor and uses the filling level indicator as a volume signal and
uses the current filling level indicator for the current filling level of the lungs in the steps of deriving the respective value for at least one of the model parameter of the first relationship, second relationship, or overall relationship.

12. A process in accordance with claim 1, wherein the signal processing unit splits up the overall measurable respiratory signal or the first measurable respiratory signal and the second measurable respiratory signal into
an inhalation signal component, which is generated on the basis of an inhalation (inspiration) performed by the patient, and
an exhalation signal component, which is generated on the basis of an exhalation (expiration) performed by the patient,
derives for the model parameter of the first or second or overall relationship and/or for the model parameter of the airway pressure function two respective model parameter values, namely,
an inhalation parameter value, which applies to the inhalation by the patient, and
an exhalation parameter value, which applies to the exhalation by the patient, and calculates a respective inhalation indicator component for the first pneumatic indicator and the second pneumatic with the use of the inhalation parameter values, calculates a respective exhalation indicator component for the first pneumatic indicator and the second pneumatic indicator with the use of the exhalation parameter values and determines the first pneumatic indicator and the second pneumatic indicator with the use of the respective inhalation indicator component and the respective exhalation indicator component.

13. A process in accordance with claim 1, wherein the signal processing unit uses as the airway pressure function a function, which describes a measurable indicator for a first derivation over time of the airway pressure as a function of an indicator for the volume flow and/or of a first derivation over time of the volume flow and a respective first derivation over time of the first pneumatic indicator and the second pneumatic indicator.

14. A process in accordance with claim 1, wherein at least some of the steps are triggered by a computer program while the computer program is executed on the signal processing unit, in the case that the signal processing unit receives measured values from at least one of the airway pressure sensor, the volume flow sensor, the filling level sensor and the breathing sensor.

15. A process in accordance with claim 1, wherein at least some of the steps are triggered by a signal sequence when the signal sequence being executed on the signal processing unit in the case that the signal processing unit receives measured values from at least one of the airway pressure sensor, the volume flow sensor, the filling level sensor and the breathing sensor.

16. A process in accordance with claim 1, wherein the first relationship and/or the second relationship and/or the overall relationship is a transfer function, which depends linearly on the model parameter or each model parameter, and the model parameter of the first relationship and/or the second relationship and/or the overall relationship is a proportionality factor for a proportionality between the first or second or overall pneumatic indicator and the first or second or overall measurable respiratory signal.

17. A signal processing unit for determining by calculation a first pneumatic indicator and a second pneumatic indicator for the breathing activity of a patient, wherein the first pneumatic indicator describes activity of a first region of the respiratory system of the patient and/or of a first process during breathing by the patient and the second pneumatic indicator describes activity of a second region of the respiratory system of the patient and/or of a second process during breathing by the patient, the second region being different from the first region and/or the second process being different from the first process, wherein the signal processing unit has at least temporarily reading access to a memory, in which memory, a predefined airway pressure function is stored in a computer-accessible form, wherein the airway pressure function describes a measurable indicator for an airway pressure, wherein the airway pressure is achieved by an overall intrinsic breathing activity of the patient and/or by mechanical ventilation of the patient, as a function of at least a volume flow indicator for a volume flow of breathing air relative to the patient and a filling level indicator for a filling level of the lungs of the patient as well as a function of the first pneumatic indicator and the second pneumatic indicator to be determined and/or of an overall pneumatic indicator for an overall breathing activity of the patient, wherein furthermore a predefined first relationship between the first pneumatic indicator and a first measurable respiratory signal and/or a predefined second relationship between the second pneumatic indicator and a second measurable respiratory signal and/or an overall relationship between the overall pneumatic indicator for the overall breathing activity of the patient and a measurable overall respiratory signal are stored in the memory in a computer-accessible form, wherein at least one of the predefined first and second relationships and/or the overall relationship has a model parameter and wherein the patient can be connected or is at least temporarily connected to an airway pressure sensor, which sensor is configured to measure the measurable indicator for the airway pressure, wherein the signal processing unit is configured to receive measured values from the airway pressure sensor while the patient is connected to the airway pressure sensor and to generate the airway pressure signal with the use of at least some of the values measured by the airway pressure sensor and to use a predefined value for the airway pressure as an airway pressure signal while the patient is not connected to the airway pressure sensor, wherein the signal processing unit is configured to receive values measured by a volume flow sensor during the overall intrinsic breathing activity of the patient and/or the mechanical ventilation of the patient, the volume flow sensor being configured to measure a volume flow indicator for a volume flow of breathing air, and to generate a volume flow signal from at least some of the values measured by the volume flow sensor and/or to receive values measured by a filling level sensor during the overall intrinsic breathing activity of the patient and/or the mechanical ventilation of the patient, the filling level sensor being configured to measure the filling level indicator for a filling level of the lungs, and to generate a volume signal from the at least some of the values measured by the filling level sensor, wherein the signal processing unit is configured to carry out a first and/or a second and/or a third sequence during the overall intrinsic breathing activity of the patient and/or the mechanical ventilation of the patient, wherein the first sequence comprises steps that the signal processing unit receives values measured by a first breathing sensor, wherein these measured values pertain to an indicator that is correlated with the first pneumatic indicator, generates the first measurable respiratory signal from these measured values, derives a respective value for the model parameter, which occurs in the first relationship, with the use of the airway pressure function and of generated signals, which signals occur in the airway pressure function, determines the first pneumatic indicator with the use of the first relationship and of the derived value for the model parameter occurring in the first relationship and wherein the second sequence comprises the steps that the signal processing unit receives values measured by a second breathing sensor, wherein these measured values pertain to an indicator that is correlated with the second pneumatic indicator, generates the second measurable respiratory signal from at least some of the-values by the second breathing sensor, derives a respective value for the model parameter, which occurs in the second relationship, with the use of the airway pressure function and of generated signals, which signals occur in the airway pressure function, and determines the second pneumatic indicator with the use of the second relationship and of the derived value of the model parameter occurring in the second relationship, wherein the third sequence comprises the steps that the signal processing unit receives measured values from an overall breathing sensor, wherein the measured values pertain to an indicator that is correlated with the overall pneumatic indicator, generates the overall measurable respiratory signal from at least some of the values measured by the overall breathing sensor, derives a value for the model parameter, which occurs in the overall relationship, with the use of the airway pressure function and of generated signals, which signals occur in the airway pressure function, and determines the overall pneumatic indicator with the use of the overall relationship and of the derived value of the model parameter occurring in the overall relationship, wherein in the case that one of the first pneumatic indicator or the second pneumatic indicator, and the overall pneumatic indicator have been determined but the other of the one of the first pneumatic indicator or the second pneumatic indicator has not been determined, the signal processing unit is configured to determine the other of the one of the first pneumatic indicator or the second pneumatic indicator with the use of one of the first pneumatic indicator or the second pneumatic indicator, and the overall pneumatic indicator that has already been determined then, when the one pneumatic value and the overall pneumatic value have been determined but the other pneumatic value has not been determined, in the case that the one of the first pneumatic indicator or the second pneumatic indicator has been determined but neither the overall pneumatic indicator nor the other pneumatic indicator has been determined, the signal processing unit is configured to determine the overall pneumatic indicator with the use of the already determined pneumatic indicator as well as of the volume flow signal and/or of the volume signal and/or of a predefined percentage function and to determine the other pneumatic indicator with the use of the already determined pneumatic indicator and of the overall pneumatic indicator, and in the case that the overall pneumatic indicator has been determined but neither the first pneumatic indicator nor the second pneumatic indicator have been determined, the signal processing unit is configured to determine the first pneumatic indicator and the second pneumatic indicator with the use of the overall pneumatic indicator as well as of the volume flow signal and/or of the volume signal and/or of a predefined percentage function.

18. A signal processing unit in accordance with claim 17, in combination with a ventilator, wherein the ventilator is configured to operate based on the first pneumatic indicator and/or the second pneumatic indicator.

19. A process for controlling a ventilator, the process comprising:

determining a first pneumatic indicator and a second pneumatic indicator for breathing activity of a patient, wherein the first pneumatic indicator describes activity of a first region of a respiratory system of the patient and/or of a first process during breathing by the patient, and the second pneumatic indicator describes activity of a second region of the respiratory system of the patient and/or of a second process during the breathing by the patient, the controlling process comprising the steps of:

providing a predefined airway pressure function which describes a measurable indicator for an airway pressure, where the airway pressure is achieved by overall intrinsic breathing activity and/or mechanical ventilation of the patient, the airway pressure function being predefined as a function of a volume flow indicator for the volume flow of breathing air relative to the patient and/or a filling level indicator for a filling level of lungs of the patient, the airway pressure function further being predefined as a function of the first pneumatic indicator and the second pneumatic indicator to be determined and/or of an overall pneumatic indicator for an overall breathing activity of the patient, wherein a first relationship is predefined between the first pneumatic indicator and a first measurable respiratory signal, and/or a second relationship is predefined between the second pneumatic indicator and a second measurable respiratory signal, and/or an overall relationship is predefined between the overall pneumatic indicator for the overall breathing activity of the patient and an overall measurable respiratory signal, wherein at least one of the first and second relationships or the overall relationship has a model parameter, and connecting the patient to an airway pressure sensor which measures the measurable indicator for the airway pressure;

receiving measured pressure sensor values from the airway pressure sensor;

by using measured pressure sensor values, generating an airway pressure signal while the patient is connected to the airway pressure sensor;

using a predefined value for the airway pressure as the airway pressure signal while the patient is not connected to the airway pressure sensor;

receiving measured values from a volume flow sensor, which measures the volume flow indicator for a volume flow of breathing air, and generating a volume flow signal from these measured values, and/or receiving measured values from a filling level sensor, which measures the filling level indicator for a filling level of the lungs, and generates a volume signal from these measured values;

at least one of the following three sequences is carried out, in a first sequence receiving measured values from a first breathing sensor, wherein these measured values pertain to an indicator that is correlated with the first pneumatic indicator, generating from these measured values the first measurable respiratory signal, deriving a value for the model parameter that occurs in the first relationship with the use of the airway pressure function and of generated signals which occur in the airway pressure function, and determining the first pneumatic indicator with the use of the first relationship and of the derived value of the model parameter occurring in the first relationship;

in a second sequence, receiving measured values from a second breathing sensor, wherein the measured values pertain to an indicator that is correlated with the second pneumatic indicator, generating the second measurable respiratory signal from these measured values, deriving a value for the model parameter that occurs in the second relationship with the use of the airway pressure function and of generated signals which occur in the airway pressure function, and determining the second pneumatic indicator with the use of the second relationship and of the value of the model parameter occurring in the second relationship;

or in a third sequence, receiving measured values from an overall breathing sensor, wherein the measured values pertain to an indicator that is correlated with the overall pneumatic indicator, generating the overall measurable respiratory signal from these measured values, deriving a value for the model parameter that occurs in the overall relationship with the use of the airway pressure function and of generated signals, which occur in the airway pressure function, and determining the overall pneumatic indicator with the use of the overall relationship and of the derived model parameter value;

wherein a signal processing unit is configured such that in the case that one of the first pneumatic indicator or the second pneumatic indicator and the overall pneumatic indicator have been determined, but the other of the one of the first pneumatic indicator or the second pneumatic indicator has not been determined, the signal processing unit determines the other one of the first pneumatic indicator or the second pneumatic indicator with the use of one of the first pneumatic indicator and the second pneumatic indicator, and the overall pneumatic indicator, that has already been determined, and of the determined overall pneumatic indicator;

wherein the signal processing unit is configured such that in the case that the one of the first pneumatic indicator or the second pneumatic indicator has been determined but neither the overall pneumatic indicator nor the other of the one of the first pneumatic indicator or the second pneumatic indicator has been determined, the signal processing unit determines the overall pneumatic indicator with the use of the already determined pneumatic indicator as well as of the volume flow signal, and/or of the volume signal and/or of a predefined percentage function, and determines the other of the one of the first pneumatic indicator or the second pneumatic indicator with the use of the already determined pneumatic indicator and of the overall pneumatic indicator; and wherein the signal processing unit is configured such that in the case that the overall pneumatic indicator has been determined, but neither the first pneumatic indicator nor the second pneumatic indicator has been determined, the signal processing unit determines the first pneumatic indicator and the second pneumatic indicator with the use of the overall pneumatic indicator as well as of the volume flow signal and/or of the volume signal and/or of a predefined percentage function;

operating the ventilator based on the first pneumatic indicator and/or the second pneumatic indicator.

* * * * *